US006436943B1

(12) United States Patent
Stoltefuss et al.

(10) Patent No.: US 6,436,943 B1
(45) Date of Patent: Aug. 20, 2002

(54) USE OF DIHYDROPYRIMIDINES AS MEDICAMENTS, AND NOVEL SUBSTANCES

(75) Inventors: Jürgen Stoltefuss, Haan; Siegfried Goldmann, Wuppertal; Arnold Paessens, Haan; Erwin Graef, Velbert; Stefan Lottmann, Wuppertal, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/673,581

(22) PCT Filed: Apr. 7, 1999

(86) PCT No.: PCT/EP99/02346

§ 371 (c)(1),
(2), (4) Date: Oct. 18, 2000

(87) PCT Pub. No.: WO99/54312

PCT Pub. Date: Oct. 28, 1999

(30) Foreign Application Priority Data

Apr. 18, 1998 (DE) .......................................... 198 17 265

(51) Int. Cl.[7] .................... C07D 401/04; C07D 403/04; A61K 31/519; A61K 31/506
(52) U.S. Cl. ............... 514/256; 514/211.08; 514/211.1; 514/211.15; 514/212.08; 514/217.06; 514/235.8; 514/233.8; 514/255.05; 514/269; 514/258
(58) Field of Search ................................ 544/333, 329, 544/328, 327; 514/256, 258, 269, 235.8, 211.15

(56) References Cited

U.S. PATENT DOCUMENTS

| 3,787,444 A | 1/1974 | Gosteli ........................ 260/327 |
| 3,956,395 A | 5/1976 | Meyer ......................... 260/607 |
| 4,727,073 A | 2/1988 | Takaya et al. ............... 514/252 |
| 4,822,798 A | 4/1989 | Stolefuss et al. ........... 514/255 |
| 5,247,239 A | 9/1993 | Yamamura et al. |
| 5,570,277 A | 10/1996 | Ito et al. |
| 5,638,264 A | 6/1997 | Hayashi et al. |
| 5,774,319 A | 6/1998 | Carter et al. |
| 5,929,615 A | 7/1999 | D'Angelo et al. |

FOREIGN PATENT DOCUMENTS

| EP | 0103796 | 3/1984 | ......... C07D/239/20 |
| EP | 0169712 | 1/1986 | ......... C07D/239/30 |
| JP | 5-056636 | 3/1993 | |
| JP | 9-121546 | 5/1997 | |
| WO | 9901438 | 1/1999 | ......... C07D/239/20 |

OTHER PUBLICATIONS

Adler, R., and Becker, H.–D., "Zur Slektiven Oxydation von Benzylalkoholen", Acta Chem. Scand., 15(4): 849–852 (1961).

Borrmann, D., "Umsetzungen von Diketen mit Alkoholen, Phenolen und Mercaptanen", in Houben–Weyl, Methoden der Organischen Chemie, vol. 7(4), pp. 230–232 (1968).

Fife, W. K., "Regioselective Cyanation of 3–Substituted Pyridine 1–Oxides[1]", Heterocycles,22(1): 93–96 (1984).

Glickman, S. A., and Cope, A.C., "Structure of β–Amino Derivatives of α,β–Unsaturated Lactones and Esters", J. Am. Chem. Soc., 67: 1017–1020 (Jun. 1945).

Harris, T. D., and Roth, G. P., "Ortho Lithiation via a Carbonyl Synthon", J. Org. Chem.,44(12): 2004–2007 (1979).

Jones, G., "The Knoevenagel Condensation" in Organic Reactions, vol. 15, Chapter 2, John Wiley & Sons, Inc. eds., New York, London, Sydney (1967).

Korba, B. E., and Gerin, J. L., "Use of a standardized cell culture assay to assess activities of nucleoside analogs against hepatitis B virus replication", Antiviral Res., 19: 55–70 (1992).

Miyano, M. Muraki, S., Kusunoki, T., Morita, T., and Matsui, M., "Syntheses of several new compounds related to rotenoids (benzalacetones, o–benzyloxypehylacetonitrile, and chromans)", Heterocycles Compounds, 37: 13929c (1963).

Oikawa, Y., Sugano, K., and Yonemitsu, O., "Meldrum's Acid Organic Synthesis. 2. A General and Versatile Synthesis of β–Keto Esters", J. Org. Chem., 43(10): 2087–2090 (1978).

Papadopoulos, E. P., Jarrar, A., and Issiorides, C. H., "Oxidations with Manganese Dioxide" J. Org. Chem., 31: 615–616 (Feb. 1966).

Sakamoto, T., Kaneda, S., Nishimura, S. and Yamanaka, H., "Site–Selective in the Cyanation of 3–Substituted Pyridine 1–Oxides with Trimethylsilanecarbonitrile", Chem. Pharm. Bull., 33(2): 565–571 (1985).

Sells, M. A., Chen, M.–L., and Acs, G., "Production of Hepatitis B Virus Particles in Hep G2 Cells Transfected with Cloned Hepatitis B Virus DNA", Proc. Natl. Acad. Sci. USA, 84: 1005–1009 (Feb. 1987).

Primary Examiner—John M. Ford
(74) Attorney, Agent, or Firm—Jerrie L. Chiu

(57) ABSTRACT

The invention relates to dihydropyrimidines of the general formula

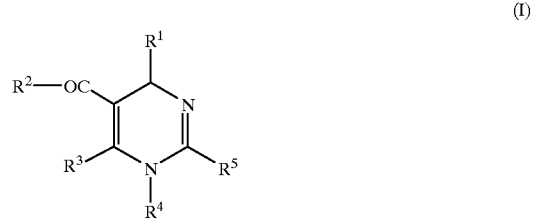

(I)

and to the use of dihydropyrimidines as medicaments for the treatment and prophylaxis of hepatitis B. The invention further relates to a process for the preparation of medicaments comprising the corresponding dihydropyrimidines.

4 Claims, No Drawings

USE OF DIHYDROPYRIMIDINES AS MEDICAMENTS, AND NOVEL SUBSTANCES

The present invention relates to the use of dihydropyrimidines as medicaments, to novel substances, to processes for their preparation, in particular as medicaments for the treatment and prophylaxis of hepatitis B.

The publication EP 103 796 A2 already discloses dihydropyrimidines having a circulation-influencing effect.

Surprisingly, it has now been found that dihydropyrimidines of the general formula (I)

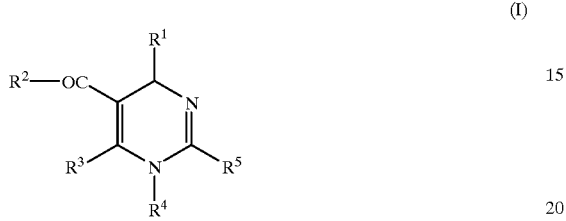
(I)

or their mesomeric form (Ia)

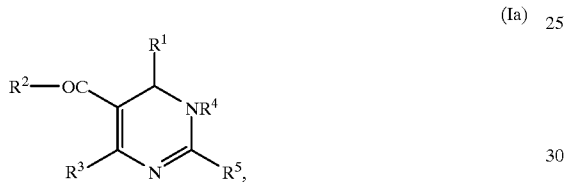
(Ia)

in which
$R^1$ is phenyl, furyl, thienyl, triazolyl, pyridyl, cycloalkyl having from 3 to 6 carbon atoms or is a radical of the formula

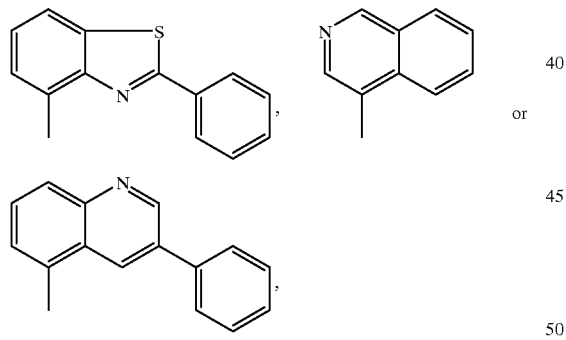

where the abovementioned ring systems are optionally mono- or polysubstituted, identically or differently, by substituents chosen from the group consisting of halogen, trifluoromethyl, nitro, cyano, trifluoromethoxy, carboxyl, hydroxyl, $(C_1-C_6)$-alkoxy, $(C_1-C_6)$-alkoxycarbonyl and $(C_1-C_6)$-alkyl which in turn can be substituted by aryl having from 6 to 10 carbon atoms or halogen,
and/or the above ring systems are optionally substituted by groups of the formulae $—S—R^6$, $NR^7R^8$, $CO—NR^9R^{10}$, $SO_2—CF_3$ and $—A—CH_2—R^{11}$,
wherein
$R^6$ is phenyl, which is optionally substituted by halogen,
$R^7$, $R^8$, $R^9$ and $R^{10}$ are identical or different and are hydrogen, phenyl, hydroxy-substituted phenyl, hydroxyl, $(C_1-C_6)$-acyl or $(C_1-C_6)$-alkyl, which for its part may be substituted by hydroxyl, $(C_1-C_6)$-alkoxycarbonyl, phenyl or hydroxy-substituted phenyl,
A is a radical O, S, SO or $SO_2$,
$R^{11}$ is phenyl, which is optionally mono- or polysubstituted, identically or differently, by substituents chosen from the group consisting of halogen, nitro, trifluoromethyl, $(C_1-C_6)$-alkyl and $(C_1-C_6)$-alkoxy,
$R^2$ is a radical of the formula $—XR^{12}$ or $—NR^{13}R^{14}$, wherein
X is a bond or oxygen,
$R^{12}$ is hydrogen, straight-chain or branched $(C_1-C_6)$-alkoxycarbonyl or a straight-chain, branched or cyclic, saturated or unsaturated $(C_1-C_8)$-hydrocarbon radical, which optionally contains one or two identical or different hetero chain members from the group consisting of O, CO, NH, $—NH—(C_1-C_4)$-alkyl, $—N—((C_1-C_4)$-alkyl$)_2$, S and $SO_2$, and which is optionally substituted by halogen, nitro, cyano, hydroxyl, aryl having from 6 to 10 carbon atoms or aralkyl having from 6 to 10 carbon atoms, heteroaryl or a group of the formula $—NR^{15}R^{16}$,
wherein
$R^{15}$ and $R^{16}$ are identical or different and are hydrogen, benzyl or $(C_1-C_6)$-alkyl,
$R^{13}$ and $R^{14}$ are identical or different and are hydrogen, $(C_1-C_6)$-alkyl or cycloalkyl having from 3 to 6 carbon atoms,
$R^3$ is hydrogen, amino or is a radical of the formula

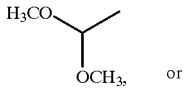 or is formyl, cyano, hydroxy-substituted $(C_1-C_6)$-alkylthio, trifluoromethyl or pyridyl, or
is a straight-chain, branched or cyclic, saturated or unsaturated hydrocarbon radical having up to 8 carbon atoms, which is optionally mono- or polysubstituted, identically or differently, by aryloxy having from 6 to 10 carbon atoms, azido, halogen, cyano, hydroxyl, carboxyl, $(C_1-C_6)$-alkoxycarbonyl, a 5- to 7-membered heterocyclic ring, $(C_1-C_6)$-alkylthio or $(C_1-C_6)$-alkoxy, which for its part can be substituted by azido or amino, and/or is substituted by triazolyl, which for its part can be substituted up to 3 times by $(C_1-C_6)$-alkoxycarbonyl,
and/or can be substituted by groups of the formula $—OSO_2—CH_3$ or $(CO)_a—NR^{17}R^{18}$,
wherein
a is a number 0 or 1,
$R^{17}$ and $R^{18}$ are identical or different and are hydrogen or aryl, aralkyl having from 6 to 10 carbon atoms,
or are $(C_1-C_6)$-alkyl, which is optionally substituted by $(C_1-C_6)$-alkoxycarbonyl, amino, hydroxyl, phenyl or benzyl, where phenyl or benzyl are optionally mono- or polysubstituted, identically or differently, by hydroxyl, carboxyl, $(C_1-C_6)$-alkyl or $(C_1-C_6)$-alkoxy,
or $(C_1-C_6)$-alkyl is optionally substituted by groups of the formula $NH—CO—CH_3$ or $NH—CO—CF_3$,
or
$R^{17}$ and $R^{18}$ together with the nitrogen atom form a morpholine, piperidinyl or pyrrolidinyl ring, or R³ is phenyl, which is optionally substituted by methoxy, or R² and R³ together form a radical of the formula

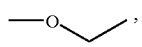

R⁴ is hydrogen, $(C_1-C_4)$-alkyl, $(C_1-C_4)$-alkenyl, benzoyl or is acyl having from 2 to 6 carbon atoms, R⁴ is hydrogen, methyl, benzoyl or is $(C_2-C_6)$-acyl, R⁵ is pyridyl, pyrimidyl or pyrazinyl, and their salts, surprisingly have an antiviral action against hepatitis B (HBV) and are therefore suitable for the prophylaxis and control of virus-induced illnesses, in particular of acutely and chronically persistent HBV virus infections.

For the purposes of the invention, cycloalkyl having from 3 to 6 carbon atoms is cyclopropyl, cyclopentyl, cyclobutyl or cyclohexyl. The following may be mentioned in preference: cyclopentyl or cyclohexyl.

Aryl is generally an aromatic radical having from 6 to 10 carbon atoms. Preferred aryl radicals are phenyl and naphthyl.

For the purposes of the invention, $(C_1-C_6)$-acyl is a straight-chain or branched acyl radical having from 1 to 6 carbon atoms. Preference is given to a straight-chain or branched acyl radical having 1 to 4 carbon atoms. Particularly preferred acyl radicals are acetyl and propionyl.

For the purposes of the invention, $(C_1-C_6)$-alkyl is a straight-chain or branched alkyl radical having 1 to 6 carbon atoms. Examples which may be given are: methyl, ethyl, propyl, isopropyl, tert-butyl, n-pentyl and n-hexyl. Preference is given to a straight-chain or branched alkyl radical having from 1 to 4 carbon atoms.

For the purposes of the invention, $(C_2-C_6)$-alkenyl is a straight-chain or branched alkenyl radical having from 2 to 6 carbon atoms. Examples which may be given are: ethenyl, propenyl, isopropenyl, tert-butenyl, n-pentenyl and n-hexenyl. Preference is given to a straight-chain or branched lower alkenyl radical having from 3 to 5 carbon atoms.

For the purposes of the invention, $(C_1-C_6)$-alkoxy is a straight-chain or branched alkoxy radical having from 1 to 6 carbon atoms. Examples which may be given are: methoxy, ethoxy, propoxy, isopropoxy, tert-butoxy, n-pentoxy and n-hexoxy. Preference is given to a straight-chain or branched alkoxy radical having from 1 to 4 carbon atoms.

For the purposes of the invention, $(C_1-C_6)$-alkoxycarbonyl is a straight-chain or branched alkoxycarbonyl radical having from 1 to 6 carbon atoms. Examples which may be given are: methoxycarbonyl, ethoxycarbonyl, propoxycarbonyl, isopropoxycarbonyl, tert-butoxycarbonyl, n-pentoxycarbonyl and n-hexoxycarbonyl. Preference is given to a straight-chain or branched alkoxycarbonyl radical having from 1 to 4 carbon atoms.

Preference is given to using compounds of the general formula (I) or (Ia)

in which

R¹ is phenyl, furyl, thienyl, triazolyl, pyridyl, cyclopentyl or cyclohexyl or is a radical of the formula

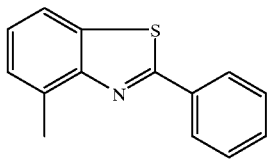, 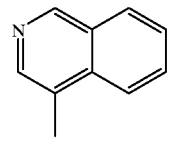 or

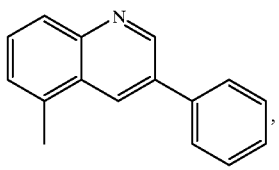, where the abovementioned ring systems are optionally mono- or disubstituted, identically or differently, by substituents chosen from the group consisting of halogen, trifluoromethyl, nitro, $SO_2$—$F_3$, methyl, cyano, trifluoromethoxy, hydroxyl, carboxyl, methoxycarbonyl or radicals of the formula —CO—NH—$CH_2$—$C(CH_3)_3$, —CO—NH—$(CH_2)_2$OH, —CO—NH—$CH_2$—$C_6H_5$, —CO—NH—$C_6H_5$, —CO—NH—(pOH)—$C_6H_4$, —O—$CH_2$—$C_6H_5$ or —S—pCl—$C_6H_4$, R² is a radical of the formula —$XR^{12}$ or —$NR^{13}R^{14}$, wherein X is a bond or an oxygen atom, R¹² is hydrogen, $(C_1-C_4)$-alkenyl, $(C_1-C_4)$-alkoxycarbonyl or $(C_1-C_4)$-alkyl which are optionally substituted by pyridyl, cyano, phenoxy, benzyl or by a radical of the formula —$NR^{15}R^{16}$, wherein R¹⁵ and R¹⁶ are identical or different and are hydrogen, benzyl or $(C_1-C_4)$-alkyl, R¹³ and R¹⁴ are identical or different and are hydrogen, $(C_1-C_4)$-alkyl or cyclopropyl, R³ is hydrogen, amino or a radical of the formula

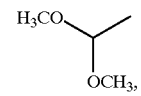

or is formyl, cyano, hydroxy-substituted $(C_1-C_4)$-alkylthio, trifluoromethyl, cyclopropyl or pyridyl, or is $(C_1-C_4)$-alkyl, which is optionally substituted by halogen, $(C_1-C_4)$-alkoxycarbonyl, hydroxyl or by triazolyl, which for its part can be substituted up to 3 times by $(C_1-C_4)$-alkoxycarbonyl, and/or alkyl is optionally substituted by groups of the formula —$OSO_2$—$CH_3$ or $(CO)_a$—$NR^{17}R^{18}$, wherein a is a number 0 or 1, R¹⁷ and R¹⁸ are identical or different and are hydrogen, phenyl or benzyl, or are $C_1-C_4$-alkyl, which is optionally substituted by $(C_1-C_4)$-alkoxycarbonyl, amino, hydroxyl, phenyl or benzyl, where phenyl or benzyl are optionally mono- or polysubstituted, identically or differently, by hydroxyl, carboxyl, $(C_1-C_4)$-alkyl or $(C_1-C_4)$-alkoxy, and/or $(C_1-C_4)$-alkyl is optionally substituted by radicals of the formula —NH—CO—$CH_3$ or —NH—CO—$CF_3$, or R¹⁷ and R¹⁸ together with the nitrogen atom form a morpholine, piperidinyl or pyrrolidinyl ring, or $R^3$ is phenyl, which is optionally substituted by methoxy, or $R^2$ and $R^3$ together form a radical of the formula

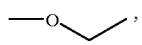

$R^4$ is hydrogen, methyl, vinyl or acetyl, and, $R^5$ is pyridyl, pyrimidyl or pyrazinyl, and their salts in the control and prophylaxis of hepatitis B.

Particular preference is given to using compounds of the general formulae (I) and (Ia), in which $R^1$ is phenyl, furyl, thienyl, triazolyl, pyridyl, cyclopentyl, cyclohexyl or is a radical of the formula

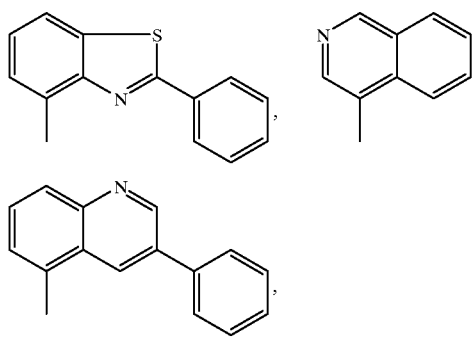

where the abovementioned ring systems are optionally substituted up to twice, identically or differently, by substituents chosen from the group consisting of fluorine, chlorine, bromine, iodine, hydroxyl, trifluoromethyl, nitro, $SO_2$—$CF_3$, methyl, cyano, trifluoromethoxy, carboxyl, methoxycarbonyl or radicals of the formula —CO—NH—$CH_2$—C($CH_3$)$_3$, —CO—NH($CH_2$)$_2$OH, —CO—NH—$CH_2$—$C_6H_5$, —CO—NH($C_6H_5$), —CO—NH—(pOH)—$C_6H_4$, —O—$CH_2$—$C_6H_5$ or —S—pCl—$C_6H_4$, $R^2$ is a radical of the formula —$XR^{12}$ or —$NR^{13}R^{14}$, wherein X is a bond or an oxygen atom, $R^{12}$ is hydrogen, ($C_1$–$C_3$)-alkenyl, ($C_1$–$C_4$)-alkoxycarbonyl or ($C_1$–$C_4$)-alkyl, which are optionally substituted by pyridyl, cyano, phenoxy, benzyl or by a radical of the formula —$NR^{15}R^{16}$, wherein $R^{15}$ and $R^{16}$ are identical or different and are hydrogen or methyl, $R^{13}$ and $R^{14}$ are identical or different and are hydrogen, ($C_1$–$C_3$)-alkyl or cyclopropyl, $R^3$ is hydrogen, amino or is a radical of the formula

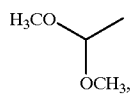

or is formyl, cyano, hydroxy-substituted ($C_1$–$C_4$)-alkylthio, trifluoromethyl, cyclopropyl or pyridyl, or is ($C_1$–$C_4$)-alkyl, which is optionally substituted by fluorine, chlorine, ($C_1$–$C_3$)-alkoxycarbonyl, hydroxyl or by triazolyl, which for its part can be substituted up to 3 times by ($C_1$–$C_3$)-alkoxycarbonyl, and/or alkyl is optionally substituted by groups of the formula —$OSO_2$—$CH_3$ or $(CO)_a$—$NR^{17}R^{18}$, wherein a is a number 0 or 1, $R^{17}$ and $R^{18}$ are identical or different and are hydrogen, phenyl or benzyl, or are ($C_1$–$C_3$)-alkyl, which is optionally substituted by ($C_1$–$C_3$)-alkoxycarbonyl, amino, hydroxyl, phenyl or benzyl, where phenyl or benzyl are optionally mono- or disubstituted, identically or differently, by hydroxyl, carboxyl, ($C_1$–$C_3$)-alkyl or ($C_1$–$C_3$)-alkoxy, and/or ($C_1$–$C_4$)-alkyl is optionally substituted by radicals of the formula —NH—CO—$CH_3$ or —NH—CO—$CF_3$, or $R^{17}$ and $R^{18}$ together with the nitrogen atom form a morpholine, piperidinyl or pyrrolidinyl ring, or $R^3$ is phenyl, which is optionally substituted by methoxy, or $R^2$ and $R^3$ together form a radical of the formula

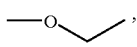

$R^4$ is hydrogen, methyl, vinyl or acetyl, and $R^5$ is pyridyl, pyrimidyl or pyrazinyl, and their salts in the control and prophylaxis of hepatitis B.

Very particular preference is given to using novel compounds of the general formulae (I) and (Ia).

in which $R^1$ is phenyl or triazolyl, which are optionally substituted up to twice, identically or differently, by fluorine, chlorine, bromine or iodine, $R^2$ is straight-chain or branched alkoxycarbonyl having up to 4 carbon atoms, $R^3$ is methyl, ethyl or cyclopropyl, or $R^2$ and $R^3$ together form a radical of the formula

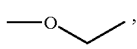

$R^4$ is hydrogen, vinyl or acetyl, and $R^5$ is pyridyl, in the prophylaxis and control of hepatitis B.

The present invention also relates to novel substances, which are listed in Table A:

TABLE A
Structure
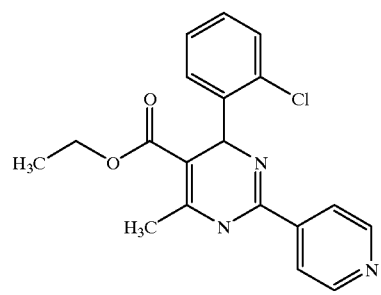
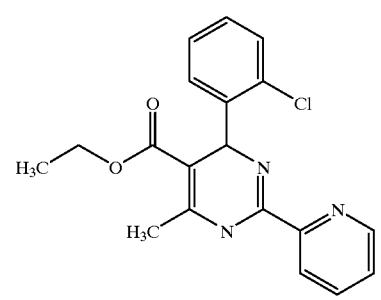
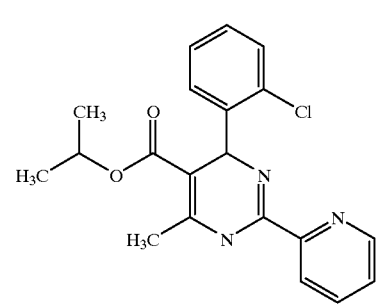
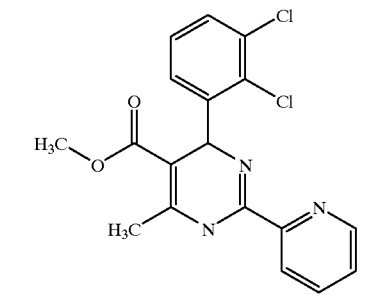
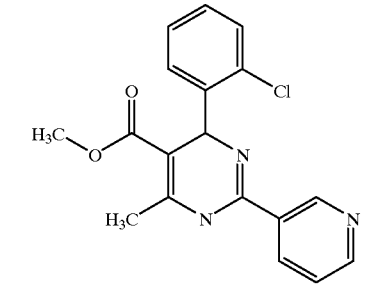
TABLE A-continued
Structure
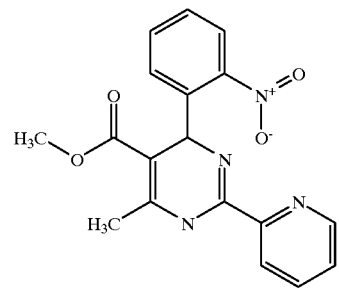
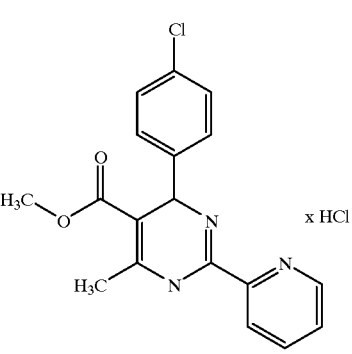
x HCl
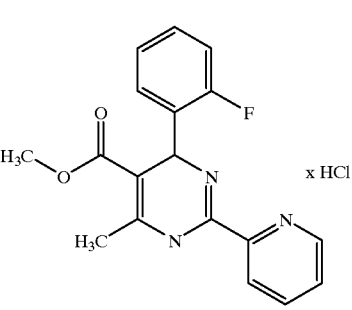
x HCl
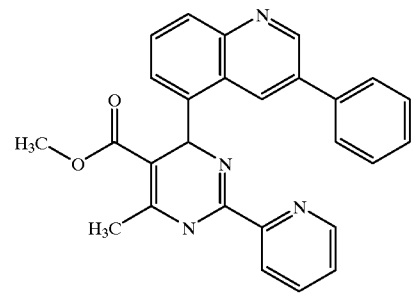
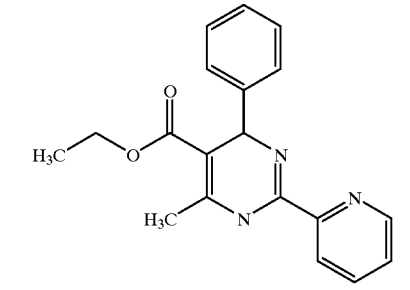

TABLE A-continued
Structure
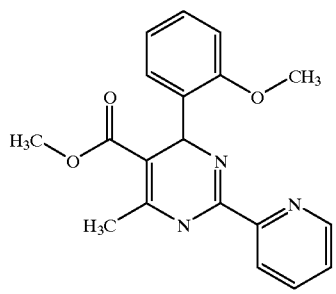
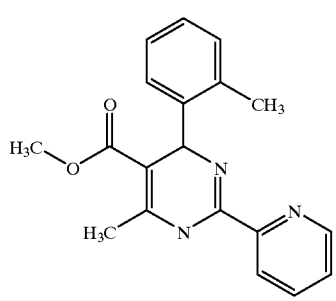
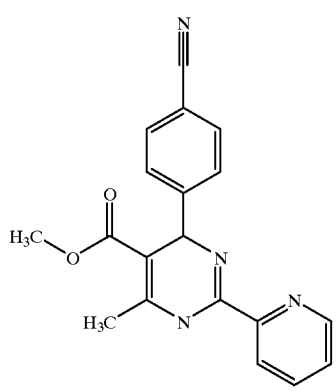
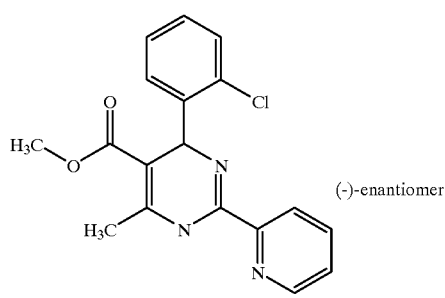
(−)-enantiomer
TABLE A-continued
Structure
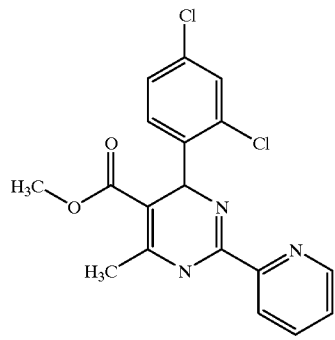
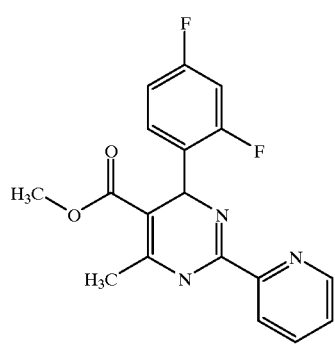
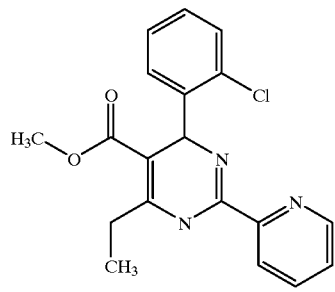
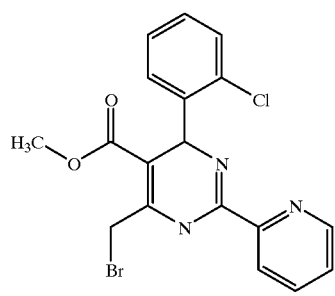

TABLE A-continued
Structure
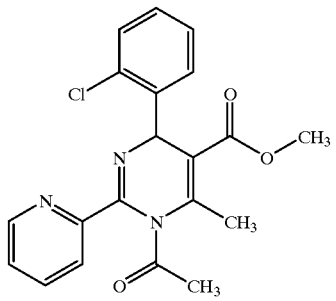
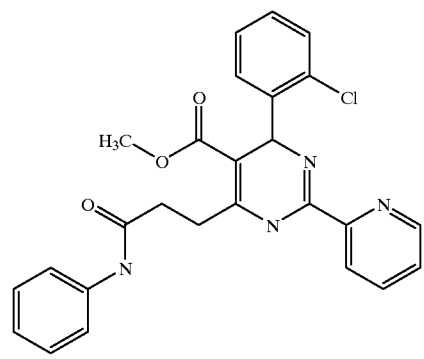
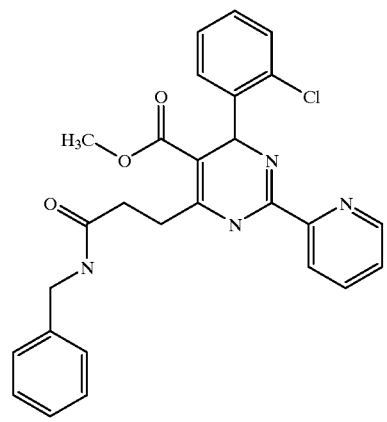
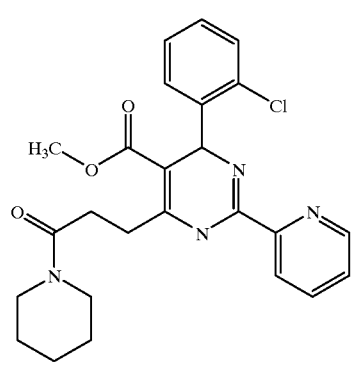
TABLE A-continued
Structure
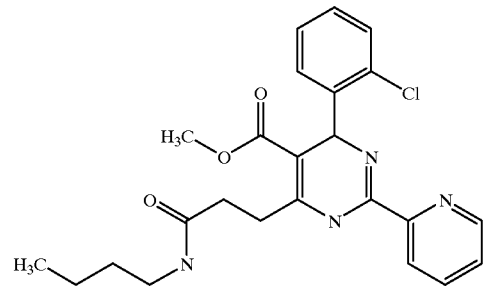
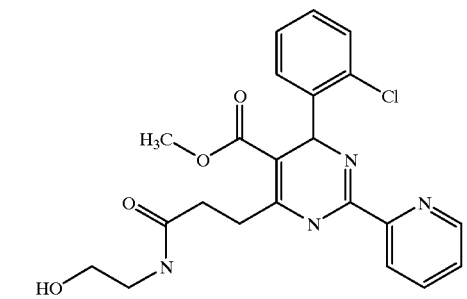
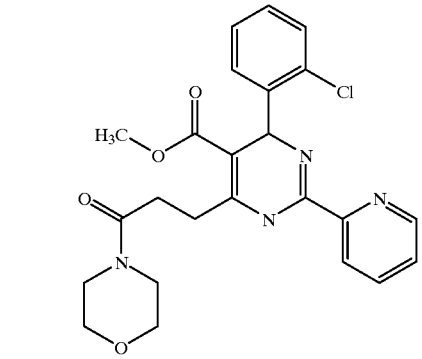
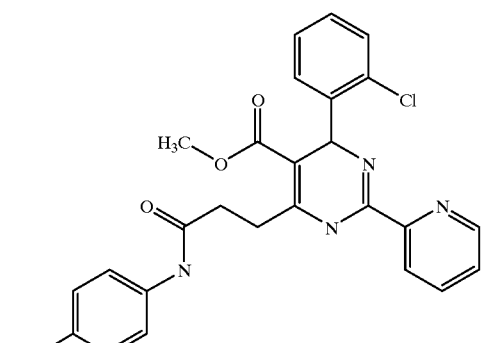

TABLE A-continued

Structure

TABLE A-continued
Structure
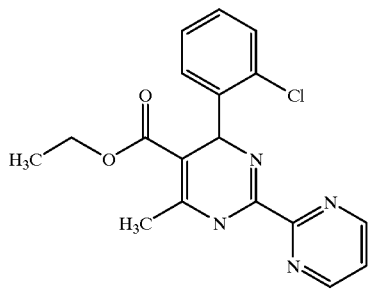
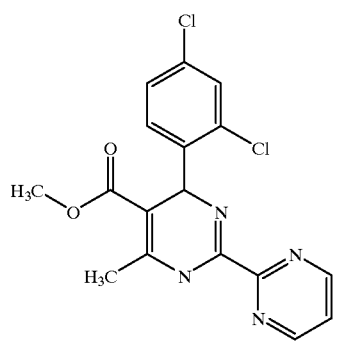
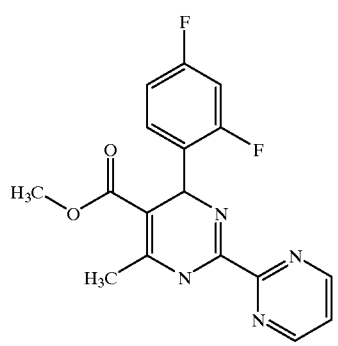
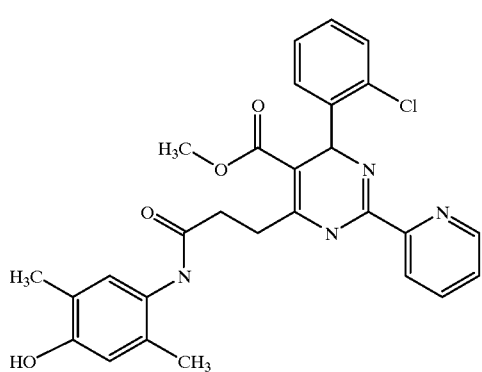
TABLE A-continued
Structure
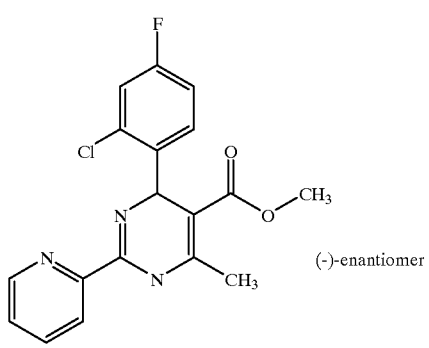
(-)-enantiomer
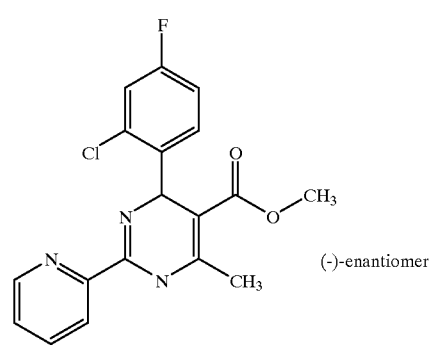
(-)-enantiomer
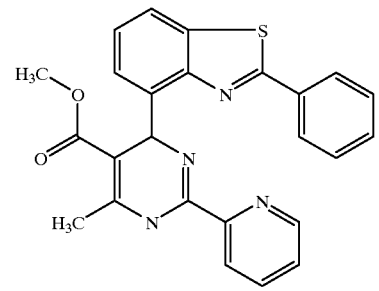
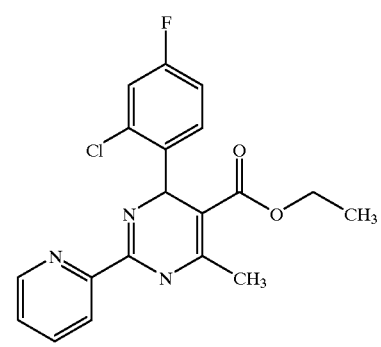

TABLE A-continued

TABLE A-continued
Structure
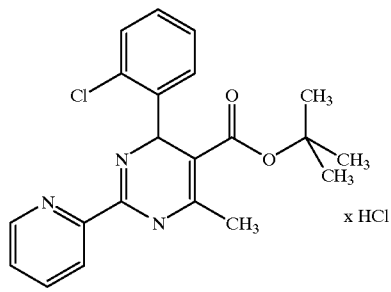 x HCl
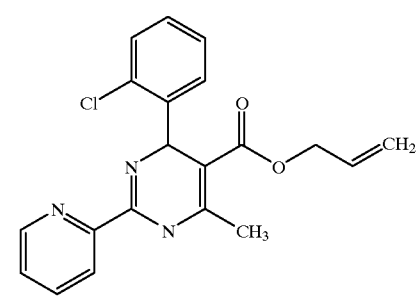
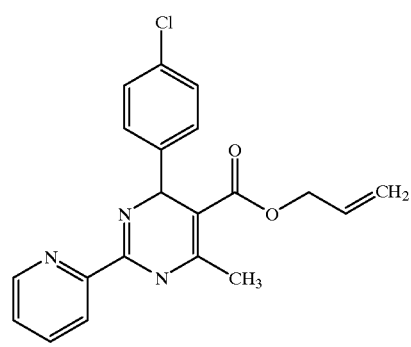
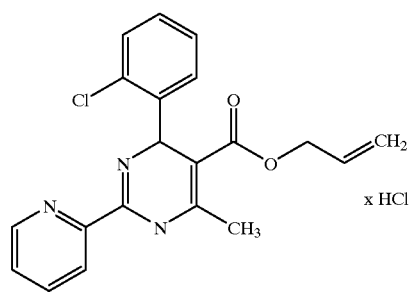 x HCl
TABLE A-continued
Structure
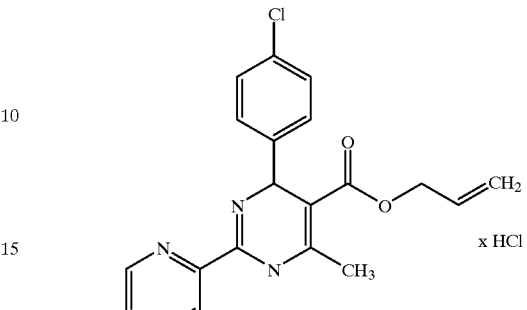 x HCl
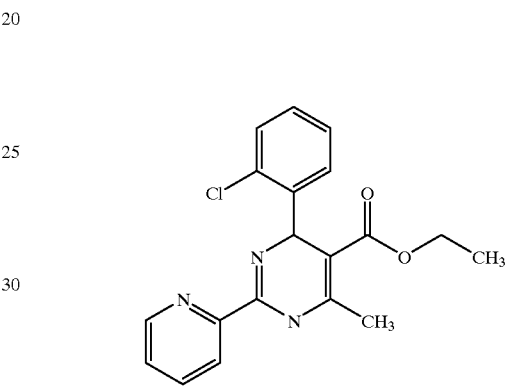
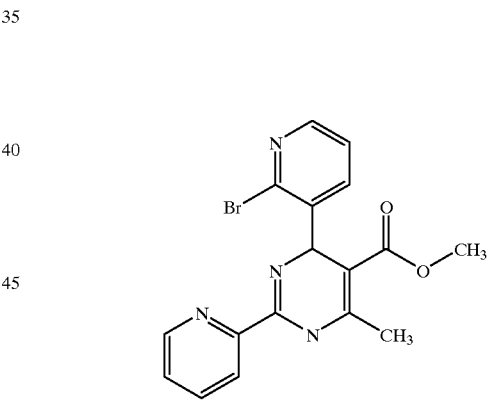
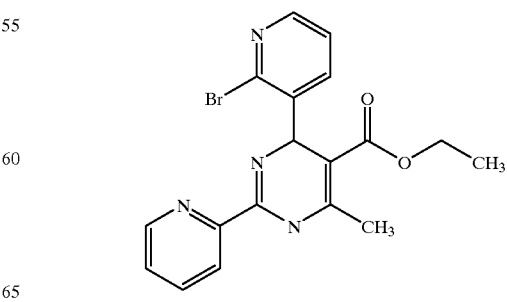

TABLE A-continued
Structure
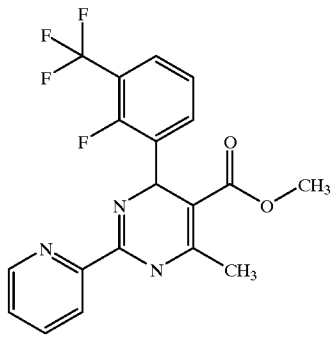
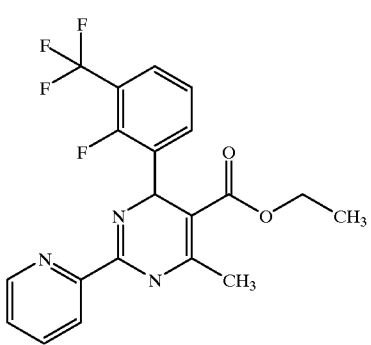
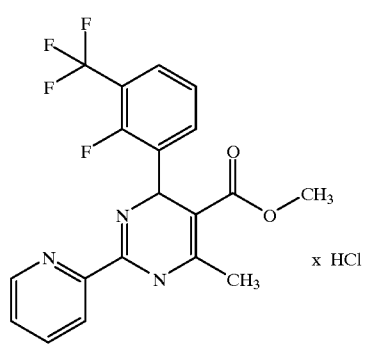
x HCl
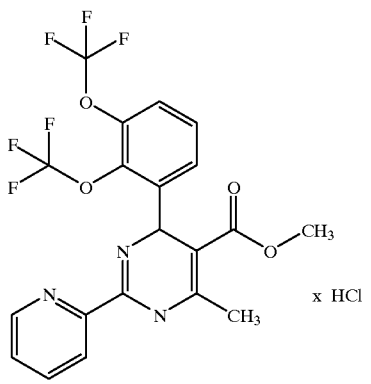
x HCl
TABLE A-continued
Structure
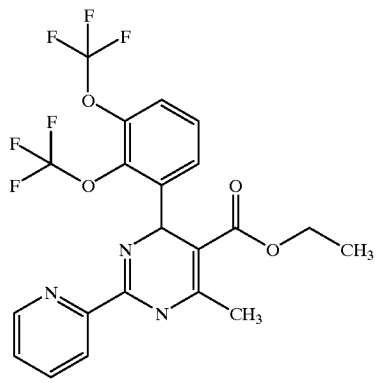
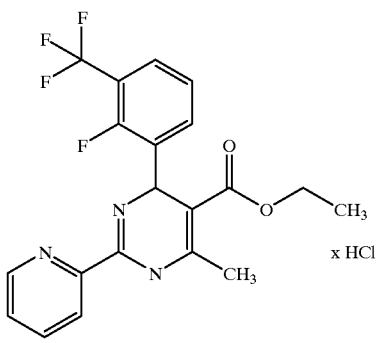
x HCl
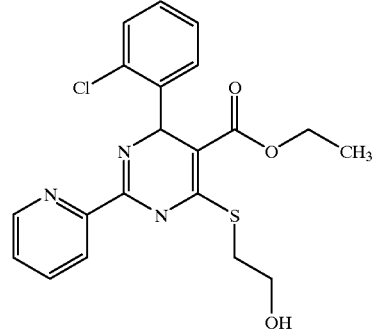
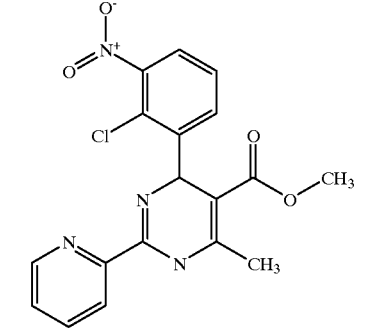

TABLE A-continued
Structure
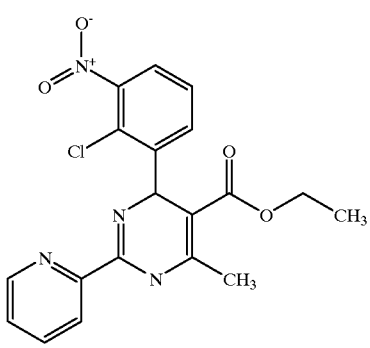
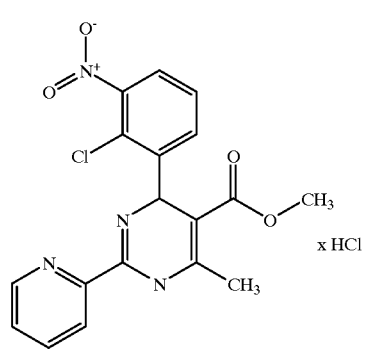
x HCl
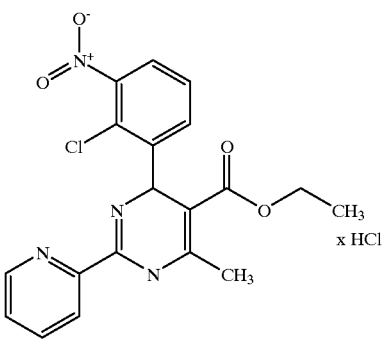
x HCl
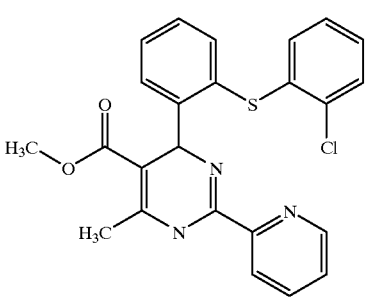
TABLE A-continued
Structure
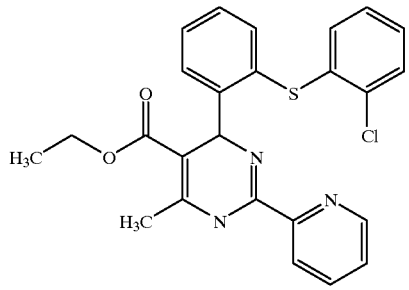
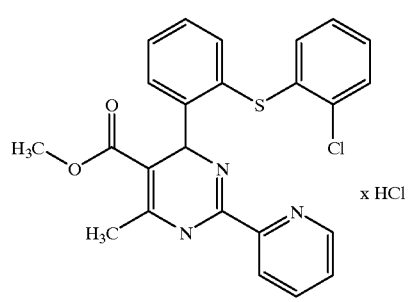
x HCl
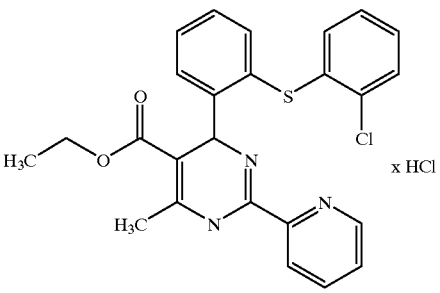
x HCl
*Unless stated otherwise, the radical  is always the  -function in the structures listed.
Preference is given to using the novel compounds which are listed in Table B.
TABLE B
Structure
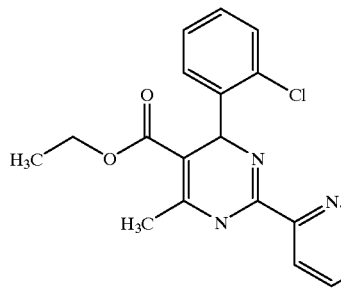

TABLE B-continued
Structure
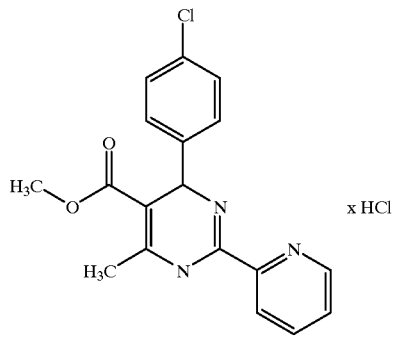
x HCl
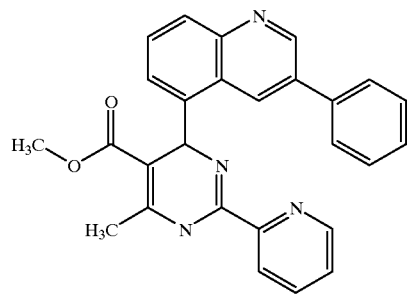
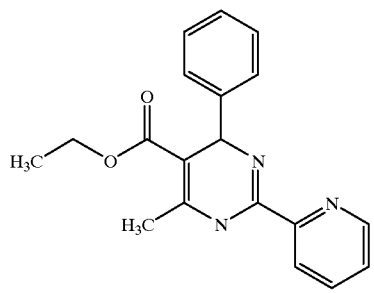
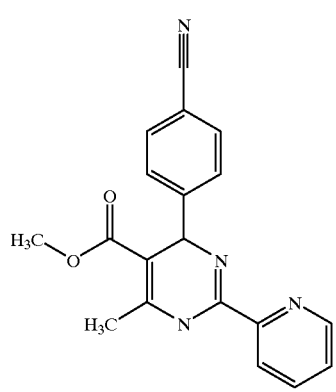
TABLE B-continued
Structure
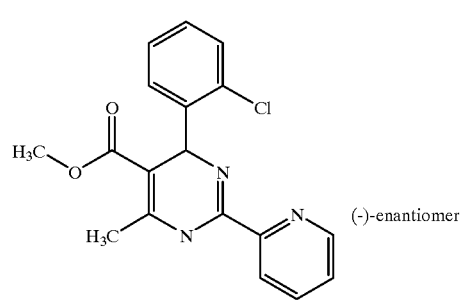
(−)-enantiomer
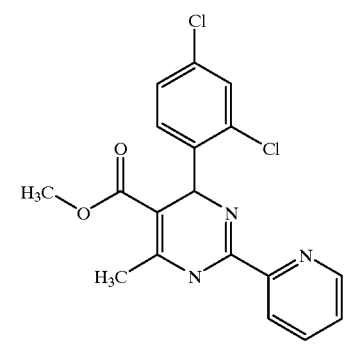
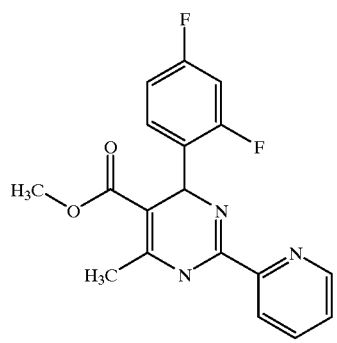
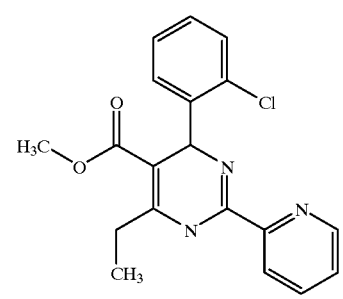

TABLE B-continued
Structure
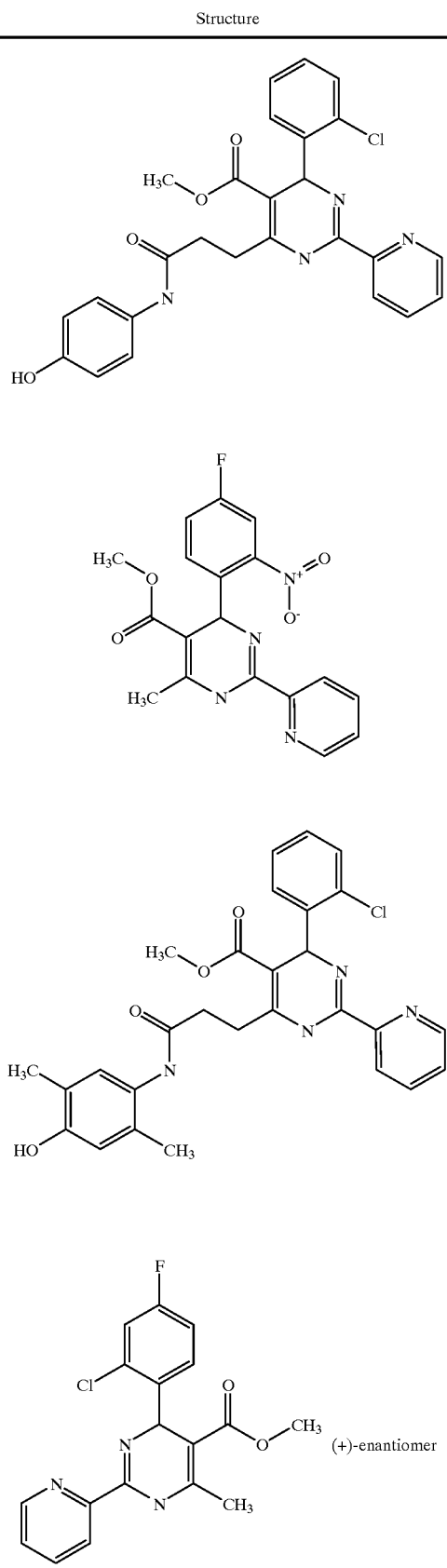
(+)-enantiomer
TABLE B-continued
Structure
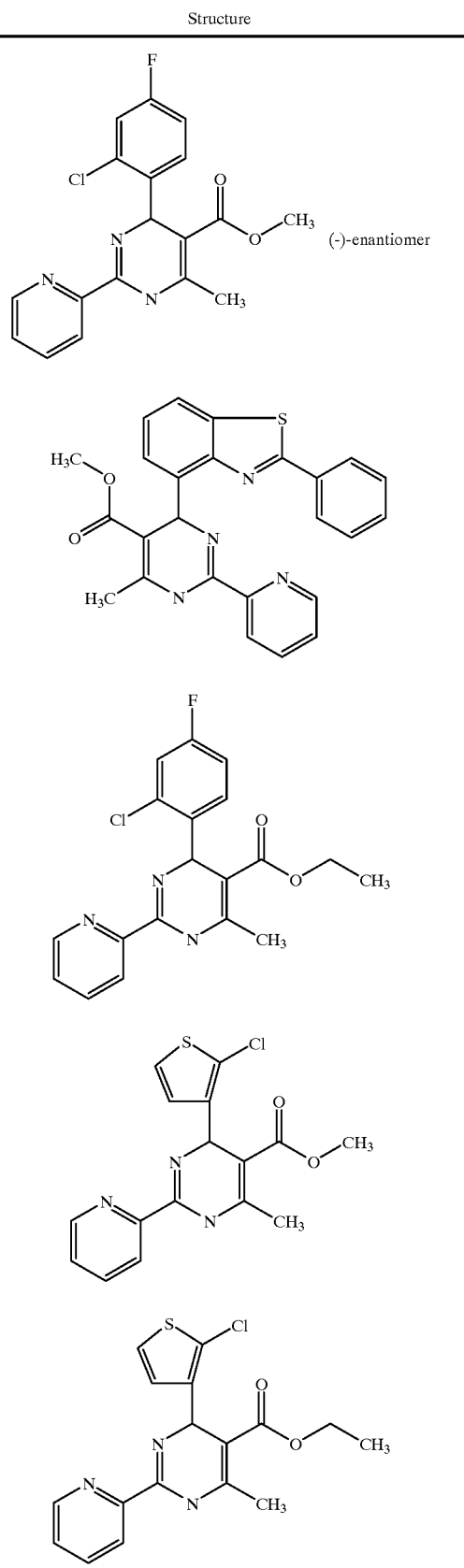
(−)-enantiomer

TABLE B-continued

Structure

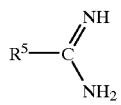

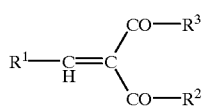

The novel compounds can exist in stereoisomeric forms, which behave either as image and mirror-image (enantiomers), or which do not behave as image and mirror-image (diastereomers). The invention relates to both the enantiomers or diastereomers or their corresponding mixtures. The racemic forms, like the diastereomers, can likewise be separated into the stereoisomerically uniform constituents by a known method.

The novel substances can also be in the form of salts. For the purposes of the invention, physiologically acceptable salts are preferable.

Physiologically acceptable salts can be salts of the novel compounds with inorganic or organic acids. Preference is given to salts with inorganic acids, such as, for example, hydrochloric acid, hydrobromic acid, phosphoric acid or sulphuric acid, or salts with organic carboxylic or sulphonic acids, such as, for example, acetic acid, maleic acid, fumaric acid, malic acid, citric acid, tartaric acid, lactic acid, benzoic acid, or methanesulphonic acid, ethanesulphonic acid, phenylsulphonic acid, toluenesulphonic acid or naphthalenedisulphonicacid.

Physiologically acceptable salts can likewise be metal or ammonium salts of the novel compounds. Particular preference is given, for example, to sodium, potassium, magnesium or calcium salts, and to ammonium salts derived from ammonia or organic amines such as, for example, ethylamine, di- or triethylamine, di- or triethanolamine, dicyclohexylamine, dimethylaminoethanol, arginine, lysine, ethylenediamine or 2-phenylethylamine.

The novel compounds of the general formulae (I) and the novel compounds (Table A) can be prepared
by reacting
[A] aldehydes of the general formula (II)

$$R^1\text{—CHO} \quad \text{(II)}$$

in which
$R^1$ is as defined above, with amidines of the formula (III)

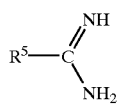

in which
$R^5$ is as defined above,
and compounds of the general formula (IV)

$$R^3\text{—CO—CH}_2\text{—CO—}R^2 \quad \text{(IV)}$$

in which
$R^2$ and $R^3$ are as defined above,
optionally in the presence of inert organic solvents with or without the addition of base or acid,
or reacting
[B] compounds of the general formula (V)

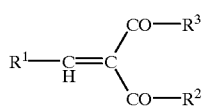

in which
$R^1$, $R^2$ and $R^3$ are as defined above,
with amidines or their hydrochlorides of the general formula (III)

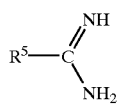

in which
$R^5$ is as defined above,
optionally in the presence of inert organic solvents at temperatures between 20° C. and 150° C. with or without the addition of base or acid,
or reacting
[C] aldehydes of the general formula (II)

$$R^1\text{—CHO} \quad \text{(II)}$$

in which
$R^1$ is as defined above,
with compounds of the general formula (VI)

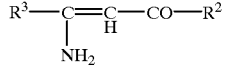

in which
$R^2$ and $R^3$ are as defined above,
and amidines of the general formula (III) as described above,
or reacting

[D] aldehydes of the general formula (II) with compounds of the general formula (IV) and imino ethers of the general formula (VII)

$$\underset{R^1-O}{\overset{HN}{\diagdown}}C-R^5 \quad (VII)$$

in which
R$^5$ is as defined above,
and
R$^1$ is (C$_1$–C$_4$)-alkyl,
in the presence of ammonium salts.

The preferred novel process [A] can be illustrated by way of example by the following equation:

[A]

[Reaction scheme showing 4-fluoro-2-chlorobenzaldehyde + ethyl acetoacetate + 2-pyridyl amidinium chloride with NaOAc yielding a dihydropyrimidine product]

For all process variants A, B, C and D, suitable solvents are all inert organic solvents. These include, preferably, alcohols, such as ethanol, methanol, isopropanol, ethers, such as dioxane, diethyl ether, tetrahydrofuran, glycol monomethyl ether, glycol dimethyl ether or acetic acid, dimethylformamide, dimethyl sulphoxide, acetonitrile, pyridine and hexamethylphosphoric triamide.

The reaction temperatures can be varied within a relatively large range. Usual temperatures are between 20 and 150° C., but preferably at the boiling temperature of the particular solvent.

The reaction can be carried out at amospheric pressure, or at increased pressures. The pressure used is generally atmospheric pressure.

The reaction can be carried out with or without the addition of base or acid, although it has been shown that, for the purposes of the invention, a reaction preferably takes place in the presence of relatively weak acids, such as, for example, acetic acid or formic acid.

The aldehydes of the general formula (II) used as starting materials are known or can be prepared by methods known from the literature [cf. T. D. Harris and G. P. Roth, J. Org. Chem. 44, 146 (1979), Deutsche Offenlegungsschrift 2 165 260, July 1972, Deutsche Offenlegungsschrift 2 401 665, July 1974, Mijano et al., Chem. Abstr. 59, (1963), 13 929 c, E. Adler and H.-D. Becker, Chem. Scand. 15, 849 (1961), E. P. Papadopoulos, M. Mardin and Ch. Issidoridis, J. Org. Chem. Soc. 78, 2543 (1956)].

The ylidene-β-keto esters of the formula (V) used as starting materials can be prepared by methods known in the literature [cf. G. Jones, "The Knoevenagel Condensation", in Organic Reactions, Vol. XV, 204 ff. (1 967)].

The enaminocarboxylic esters of the formula (VI) and the imino ethers of the general formula (VII) used as starting materials are known and can be prepared by methods known in the literature [cf. S. A. Glickman and A. C. Cope, J. Am. Chem. Soc. 67, 1017 (1945)].

The β-ketocarboxylic esters of the general formula (IV) used as starting materials are known or can be prepared by methods known in the literature [e.g. D. Borrmann, "Umsetzung von Diketen mit Alkoholen, Phenolen und Mercaptanen" [Reaction of diketenes with alcohols, phenols and mercaptans], in Houben-Weyl, Methoden der organischen Chemie, Vol. VII/4, 230 ff (1968); Y. Oikawa, K. Sugano and O. Yonemitsu, J. Org. Chem. 43, 2087 (1978)].

The compounds of the general formula (III) can be prepared by reacting compounds of the formula (VIII)

$$R^5-CN \quad (VIII)$$

in which
R$^5$ is as defined above,
as usual via the imino ethers and finally with ammonium chloride in methanol [cf. in this respect in analogy to W. K. Fife, Heterocycles 22, 93–96 (1984); T. Sakamoto, S. Kaneda, S. Nishimura, H. Yamanaka, Chem. Pharm. Bull. 33,565,571 (1986)].

All of the process steps take place at atmospheric pressure and in a temperature range from 0° C. to 130° C., preferably from 20° C. to 100° C.

The compounds of the general formula (VIII) are known per se.

The antiviral action of the novel compounds was determined in accordance with the methods described by Sells et al. (M. A. Sells, M.-L. Chen, and G. Acs (1987) Proc. Natl. Acad. Sci. 84, 1005–1009) and Korba et al. (B. E. Korba and J. L. Gerin (1992) Antiviral Research 19, 55–70).

The antiviral tests were carried out in 96-well microtitre plates. The first vertical row of plates contained only growth medium and HepG2.2.15 cells. This served as virus control.

Stock solutions of the test compounds (50 mM) were firstly dissolved in DMSO, and further dilutions were prepared in HepG2.2.15 growth medium. The novel compounds were usually pipetted in a test concentration of 100 μM (1st test concentration) in each case into the 2nd vertical test row of the microtitre plate and then diluted in doubling steps to $2^{10}$ fold in growth medium plus 2% of foetal calf serum (volume 25 μl).

Each well of the microtitre plate then contained 225 μl of a HepG2.2.15 cell suspension (5×10$^4$ cells/ml) in growth medium plus 2% of foetal calf serum.

The test batch was incubated at 37° Celsius, 5% CO$_2$, for 4 days.

The supernatant was then removed by suction and discarded, and the wells received 225 μl of freshly prepared growth medium. The novel compounds were added in each case again as 10-fold concentrated solution in a volume of 25 μl. The mixtures were incubated for a further 4 days.

Prior to harvesting the supernatants for determining the antiviral effect, the HepG2.2.15 cells were investigated for cytotoxic changes using a light microscope or using biochemical detection methods (e.g. Alamar blue stain or Trypan blue stain). The supernatants were then harvested and sucked by means of a vacuum onto 96-well dot blot chambers covered with nylon membrane (in accordance with the manufacturer's instructions).

Cytoxicity Determination

Substance-induced cytotoxic or cytostatic changes in HepG2.2.15 cells were determined as changes in cell morphology using, for example, a light microscope. Such substance-induced changes in HepG2.2.15 cells compared with untreated cells were visible, for example, as cell lysis, vacuolization or modified cell morphology. 50% cytotoxicity (Tox.–50) means that 50% of the cells have a morphology comparable with the corresponding cell control.

The compatibility of some of the novel compounds was additionally tested on other host cells, such as, for example, HeLa cells, primary peripheral human blood cells or transformed cell lines such as H-9 cells.

No cell-cytotoxic changes were found at concentrations of the novel compounds of >10 $\mu$M.

Determination of the Antiviral Action

After the supernatants had been transferred onto the nylon membrane in the blot apparatus (see above), the supernatants of the HepG2.2.15 cells were denatured (1.5 M NaCl/0.5 N NaOH), neutralized (3 M NaCl/0.5 M Tris HCl, pH 7.5) and washed (2×SSC). The DNA was then baked onto the membrane by incubating the filter at 120° C. for 2–4 hours.

Hybridization of the DNA

The detection of the viral DNA from the treated HepG2.2.15 cells on the nylon filter was usually carried out using non-radioactive, digoxigenin-labelled hepatitis B-specific DNA probes, which have each been labelled with digoxigenin, purified and used for hybridization in accordance with the manufacturer's instructions. Prehybridization and hybridization took place in 5×SSC, 1×blocking reagent, 0.1% of N-lauroylsarcosin, 0.02% of SDS and 100 $\mu$g of herring sperm DNA. The prehybridization took place for 30 minutes at 60° C., and the specific hybridization with 20–40 ng/ml of the digoxigenated, denatured HBV-specific DNA (14 hours, 60° C). The filters were then washed.

Detection of the HBV DNA by Digoxigenin Antibodies

Immunological detection of the digoxigenin-labelled DNA took place according to the manufacturer's instructions.

The filters were washed and prehybridized in a blocking reagent (according to the manufacturer's instructions). Hybridization was then carried out with an anti-DIG antibody, which had been coupled with alkaline phosphatase, for 30 minutes. After a washing step, the alkaline phosphatase substrate, CSPD, was added incubated for minutes with the filters, then packed into plastic film and incubated for a further minutes at 37° C. The chemiluminescence of the hepatitis B-specific DNA signals was made visible by exposing the filter to an X-ray film (incubation depending on the signal strength: from 10 minutes to 2 hours).

The half-maximum inhibitory concentration (IC-50, 50% inhibitory concentration) was determined as the concentration at which, compared with an untreated sample, the hepatitis B-specific band has been reduced by 50% by the novel compound.

Treatment of the hepatitis B virus-producing HepG2.2.15 cells with the novel compounds surprisingly led to a reduction in the viral DNA which is discharged into the cell culture supernatant from the cells in the form of virions in the cell culture supernatant.

The novel compounds show a novel, unforeseeable and useful effect against viruses. They have a surprising antiviral action against hepatitis B (HBV) and are thus suitable for the treatment of virus-induced diseases, in particular of acute and chronically persistent HBV viral infections. A chronic viral illness caused by HBV can lead to symptoms of varying severity; as is known, chronic hepatitis B virus infection in many cases leads to cirrhosis of the liver and/or to hepatocellular carcinoma.

Examples of indication fields for the compounds which can be useful according to the invention are:

The treatment of acute and chronic viral infections which can lead to an infectious hepatitis, for example infections with hepatitis B viruses. Particular preference is given to the treatment of chronic hepatitis B infections and the treatment of acute hepatitis B viral infection.

The present invention covers pharmaceutical preparations which, in addition to nontoxic, inert pharmaceutically suitable carriers, comprise one or more compounds of the formulae (I), (Ia) and Table A, or which consist of one or more active ingredients of the formulae (I), (Ia) and Table A, and also processes for the preparation of these preparations.

The active ingredients of formulae (I), (Ia) and Table A must be present in the abovementioned pharmaceutical preparations, preferably in a concentration of from about 0.1 to 99.5% by weight, preferably from about 0.5 to 95% by weight, of the total mixture.

The abovementioned pharmaceutical preparations can, in addition to the compounds of the formulae (I), (Ia) and Table A, also comprise further pharmaceutical active ingredients.

The abovementioned pharmaceutical preparations are prepared in a customary manner by known methods, e.g. by mixing the active ingredient(s) with the carrier(s).

Both in human and also in veterinary medicine, it is has generally proven advantageous to administer the novel active ingredient(s) in total amounts of from about 0.5 to about 500, preferably from 1 to 100, mg/Kg of bodyweight per 24 hours, optionally in the form of two or more doses, to achieve the desired results. One dose contains the active ingredient(s) preferably in amounts from about 1 to about 80, in particular from 1 to 30, mg/kg of bodyweight. It can, however, be necessary to deviate from the stated doses, depending on the nature and the bodyweight of the object to be treated, the nature and severity of the illness, the nature of the preparation and the application of the medicament, and also the period or interval within which administration takes place.

PREPARATION EXAMPLES

Example 1

Ethyl 4-(2-Chlorophenyl)-2-(pyridin-2-yl)-6-methyl-1,4-dihydro-pyrimidine-5-carboxylate

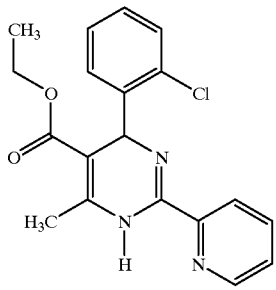

650 mg of ethyl acetoacetate, 790 mg (5 mmol) of 2-amidinopyridinium hydrochloride (Avocado e.g as supplier) and 43.06 mg of sodium acetate are added successively to 700 mg (5 mmol) of 2-chlorobenzaldehyde in 15 ml of isopropanoi, and the mixture is boiled for 6 hours. The mixture is then cooled, evaporated, dissolved in 40 ml of 0.5 N HCl and ethyl acetate and separated, and the organic phase is extracted with 10 ml of 1N HCl, and the combined aqueous phases are washed with ether. The aqueous phase is rendered basic with dilute ammonia solution and extracted with ethyl acetate; the extracted matter is washed with $H_2O$, dried and evaporated. It is dissolved in a little acetonitrile and crystallized. It is filtered off with suction, washed with acetonitrile and dried at 60° C. under reduced pressure.

TLC: pure (toluene/ethyl acetate=4:1); Yield: 750 mg (42%); m.p.: 137–138° C.

Following the instructions of Example 1, the compounds listed in Table 1 are prepared:

TABLE 1

| Ex. No. | Structure | m.p. [° C.] |
|---|---|---|
| 2 | 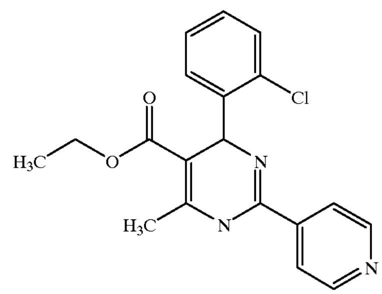 | 101–103 |
| 3 | 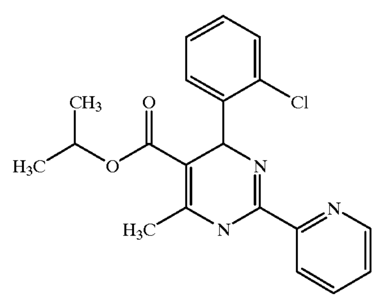 | 93–95 |
| 4 | 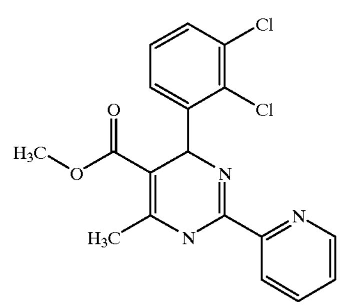 | 125–127 |

TABLE 1-continued

| Ex. No. | Structure | m.p. [° C.] |
| --- | --- | --- |
| 5 | 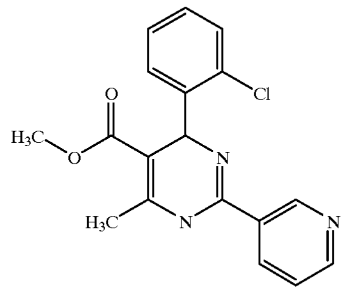 | 131–133 |
| 6 | 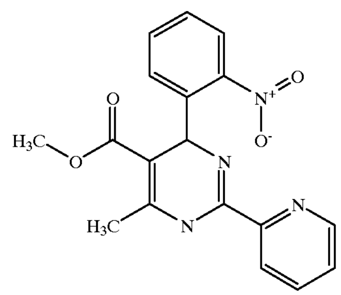 | 167–168 |
| 7 | x HCl | 201–202 |
| 8 | x HCl | 217–218 |
| 9 | 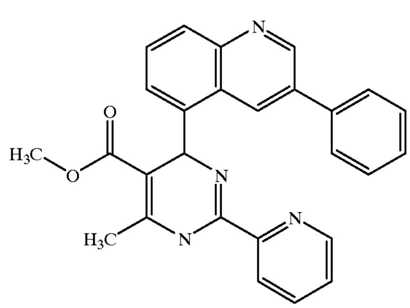 | 176–177 |

TABLE 1-continued

| Ex. No. | Structure | m.p. [° C.] |
|---|---|---|
| 10 | ethyl 4-phenyl-6-methyl-2-(pyridin-2-yl)-pyrimidine-5-carboxylate | 101–103 |
| 11 | methyl 4-(2-methoxyphenyl)-6-methyl-2-(pyridin-2-yl)-pyrimidine-5-carboxylate | 103–104 |
| 12 | methyl 4-(2-methylphenyl)-6-methyl-2-(pyridin-2-yl)-pyrimidine-5-carboxylate | 100–101 |
| 13 | methyl 4-(4-cyanophenyl)-6-methyl-2-(pyridin-2-yl)-pyrimidine-5-carboxylate | 141–143 |

TABLE 1-continued
| Ex. No. | Structure | m.p. [° C.] |
| --- | --- | --- |
| 14 | 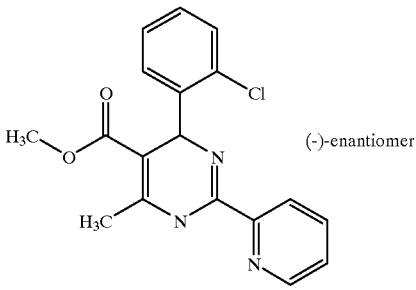 (-)-enantiomer | [α]_D = −145 (dimethylformamide) |
| 15 | 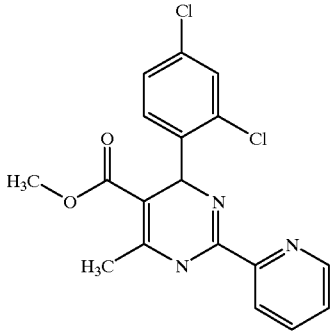 | Oil |
| 16 | 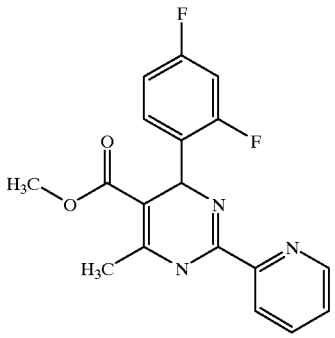 | Oil |
| 17 | 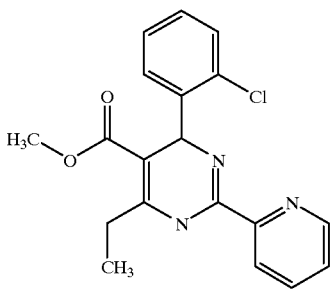 | |

TABLE 1-continued

| Ex. No. | Structure | m.p. [° C.] |
|---|---|---|
| 18 | 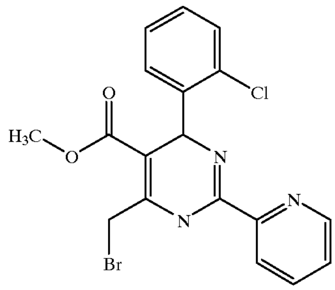 | |
| 19 | 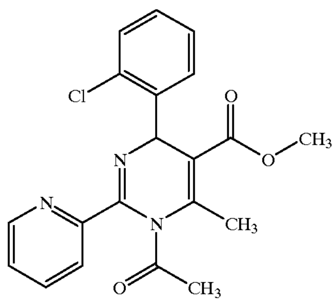 | |
| 20 | 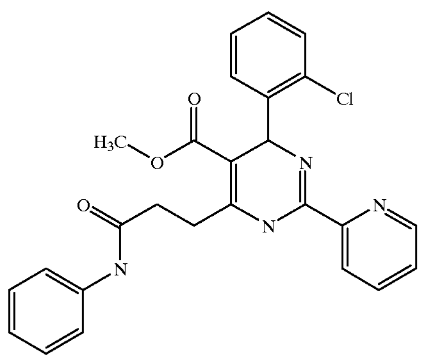 | |
| 21 | 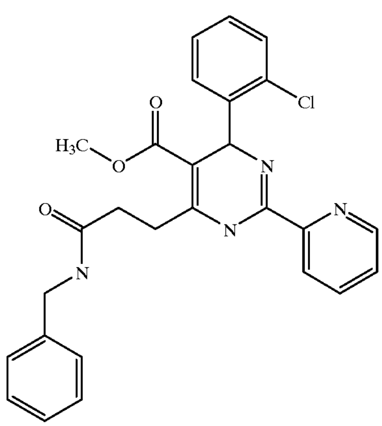 | |

TABLE 1-continued
| Ex. No. | Structure | m.p. [° C.] |
|---|---|---|
| 22 | 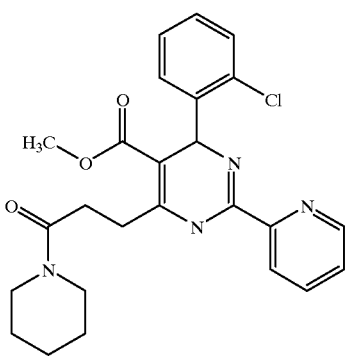 | |
| 23 | 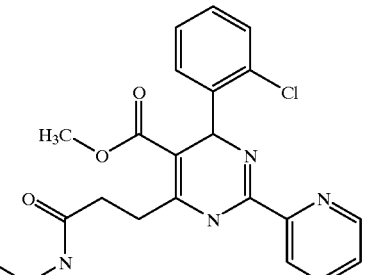 | |
| 24 | 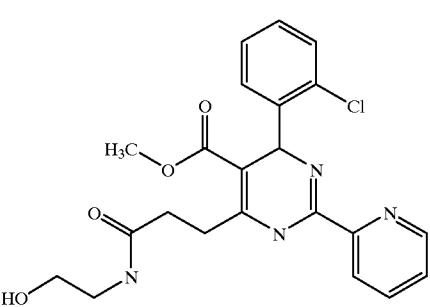 | |
| 25 | 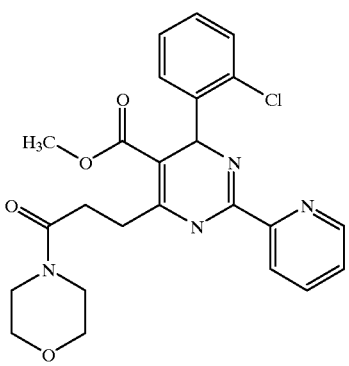 | |

TABLE 1-continued

| Ex. No. | Structure | m.p. [° C.] |
|---|---|---|
| 26 | (structure) | |
| 27 | (structure) | |
| 28 | (structure) | 175–176 |
| 29 | (structure) | 108–109 |

TABLE 1-continued

| Ex. No. | Structure | m.p. [° C.] |
| --- | --- | --- |
| 30 | 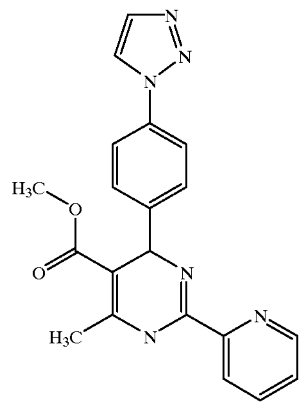 | 149–150 |
| 31 | 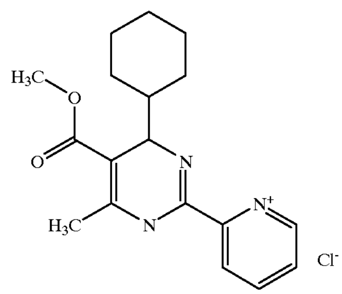 | 149–150 |
| 32 | 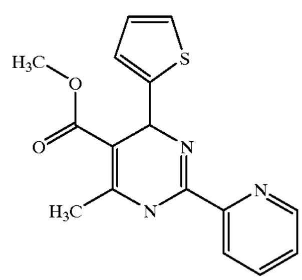 | Oil |
| 33 | 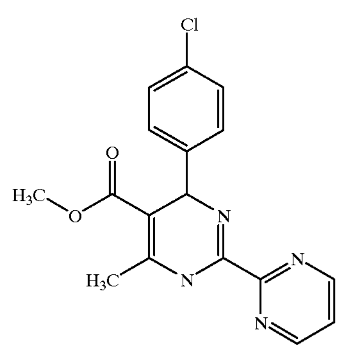 | |

TABLE 1-continued
| Ex. No. | Structure | m.p. [° C.] |
| --- | --- | --- |
| 34 | 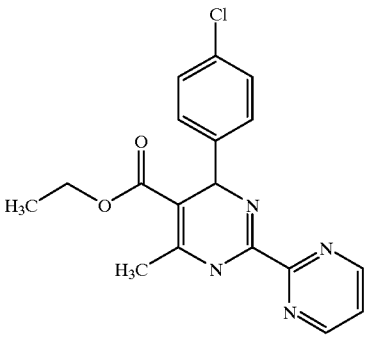 | |
| 35 | 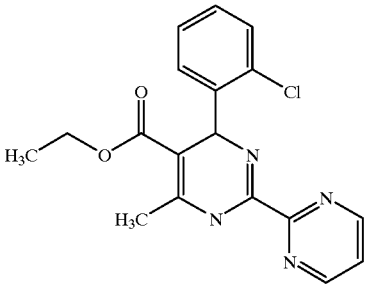 | |
| 36 | 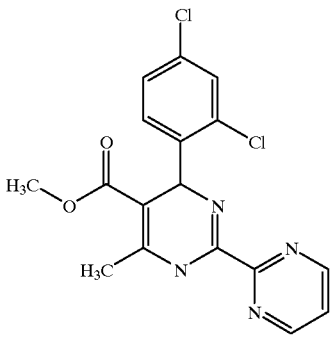 | |
| 37 | 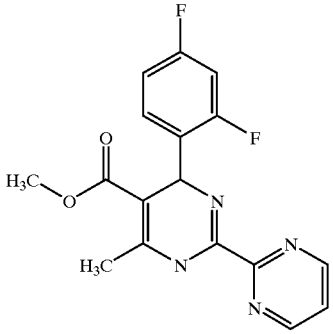 | |

TABLE 1-continued

| Ex. No. | Structure | m.p. [° C.] |
| --- | --- | --- |
| 38 | 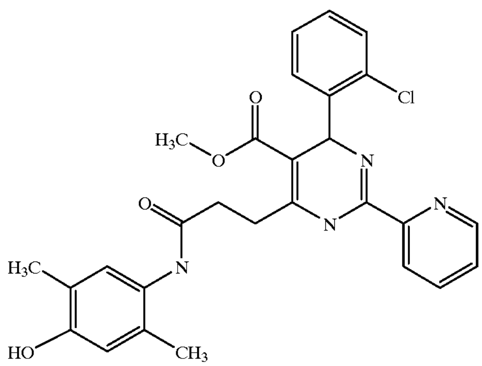 | |
| 39 | (+)-enantiomer | |
| 40 | (−)-enantiomer | |
| 41 | 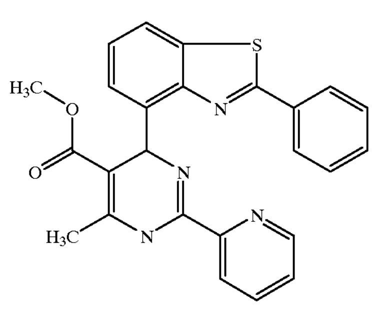 | 172–173 |

TABLE 1-continued

| Ex. No. | Structure | m.p. [° C.] |
|---|---|---|
| 42 | (4-fluoro-2-chlorophenyl; ethyl ester; methyl; pyridyl) | |
| 43 | (5-chloro-thiophen-3-yl; methyl ester; methyl; pyridyl) | |
| 44 | (2-chloro-thiophen-3-yl; ethyl ester; methyl; pyridyl) | |
| 45 | (2-chlorophenyl; n-butyl ester; methyl; pyridyl) | 176–178 |
| 46 | (2-chlorophenyl; propargyl ester; methyl; pyridyl) | |

TABLE 1-continued
| Ex. No. | Structure | m.p. [° C.] |
|---|---|---|
| 47 | 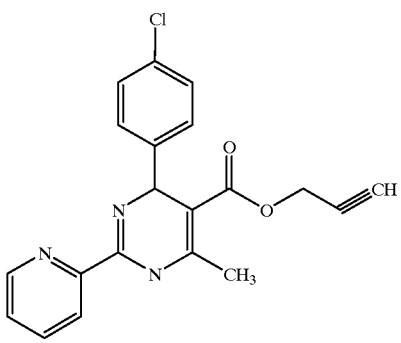 | |
| 48 | 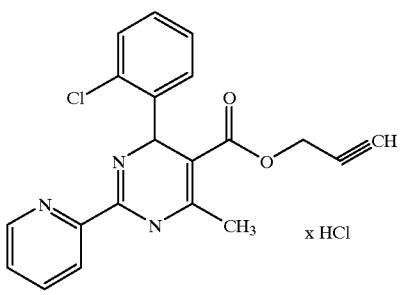 x HCl | |
| 49 | 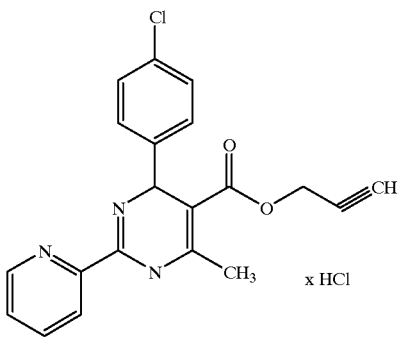 x HCl | |
| 50 | 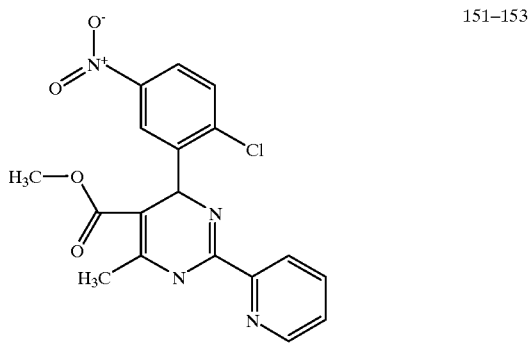 | 151–153 |

TABLE 1-continued

| Ex. No. | Structure | m.p. [° C.] |
| --- | --- | --- |
| 51 | 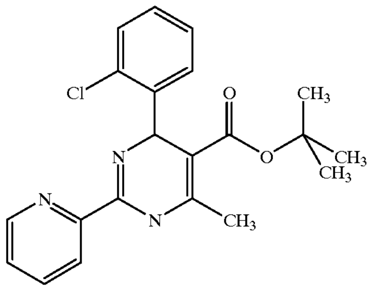 | |
| 52 | x HCl | |
| 53 | 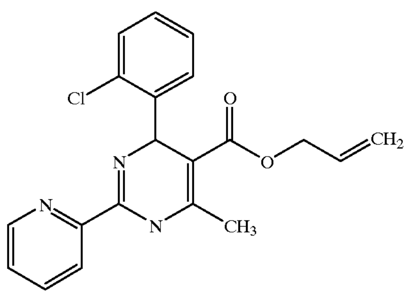 | |
| 54 | 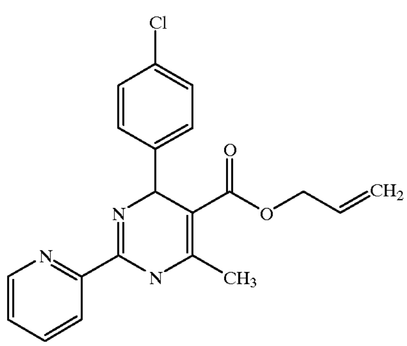 | |
| 55 | x HCl | |

TABLE 1-continued
| Ex. No. | Structure | m.p. [° C.] |
| --- | --- | --- |
| 56 | 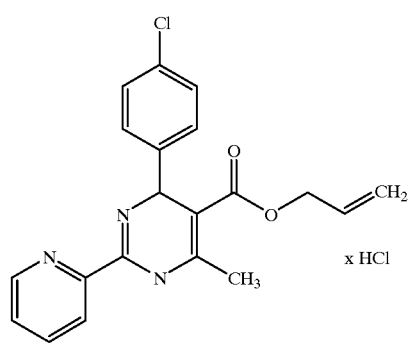 x HCl | |
| 57 | 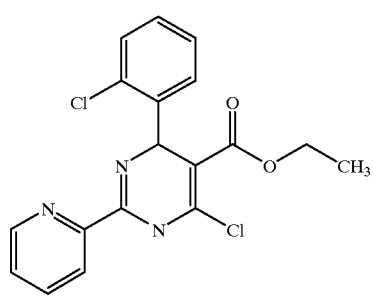 | |
| 58 | 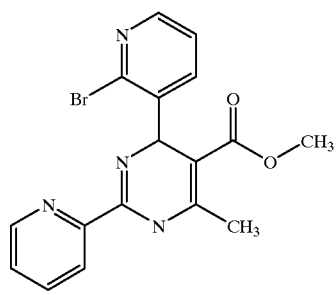 | |
| 59 | 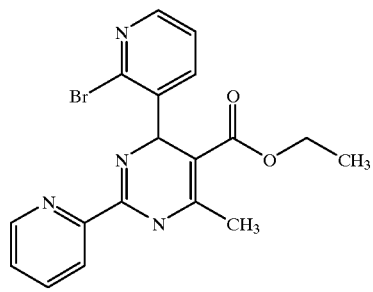 | |

TABLE 1-continued
| Ex. No. | Structure | m.p. [° C.] |
|---|---|---|
| 60 | 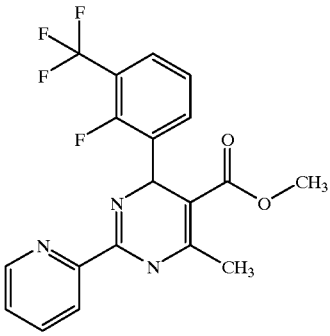 | |
| 61 | 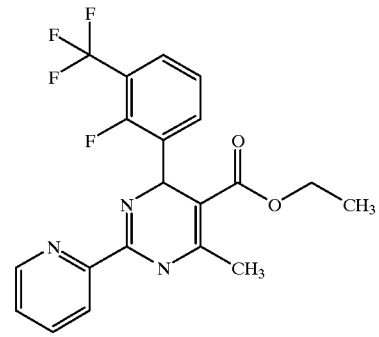 | |
| 62 | 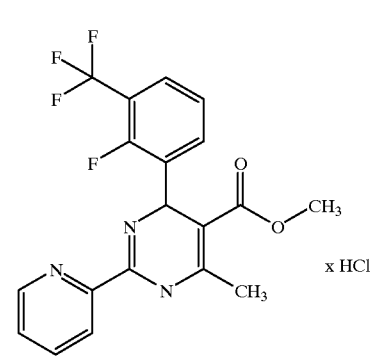 x HCl | |
| 63 | 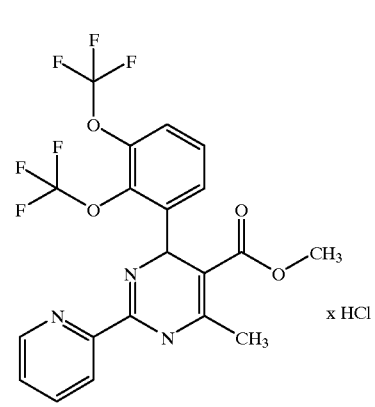 x HCl | |

TABLE 1-continued

| Ex. No. | Structure | m.p. [° C.] |
|---|---|---|
| 64 | 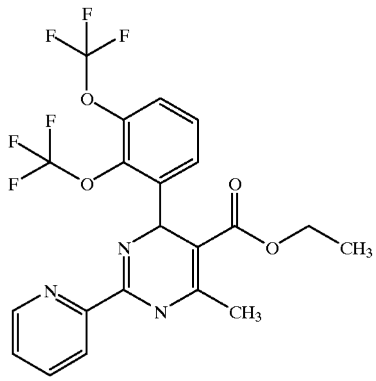 | |
| 65 | x HCl | |
| 66 | 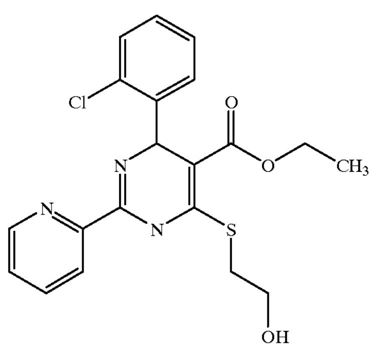 | |
| 67 | 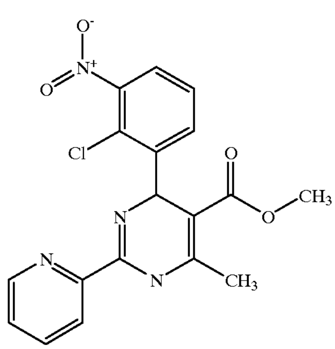 | |

TABLE 1-continued
| Ex. No. | Structure | m.p. [° C.] |
|---|---|---|
| 68 | 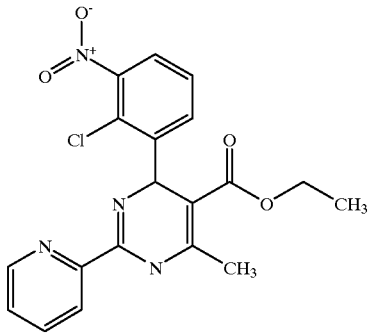 | |
| 69 | 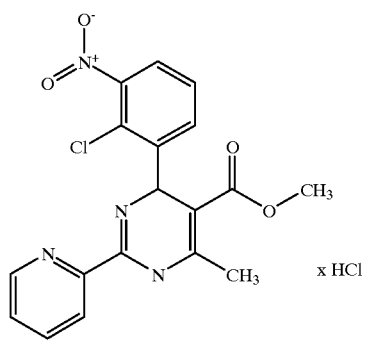 x HCl | |
| 70 | 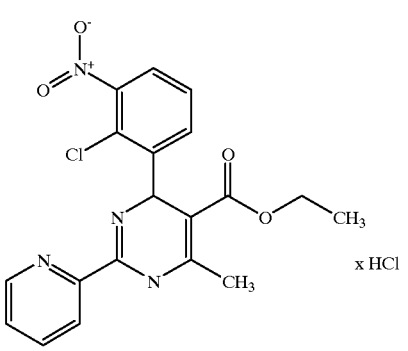 x HCl | |
| 71 | 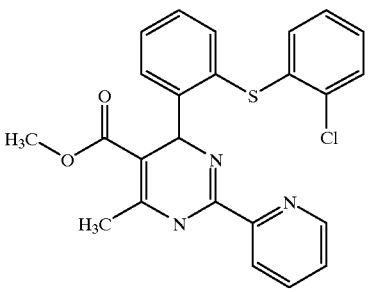 | |

TABLE 1-continued

| Ex. No. | Structure | m.p. [° C.] |
|---|---|---|
| 72 | 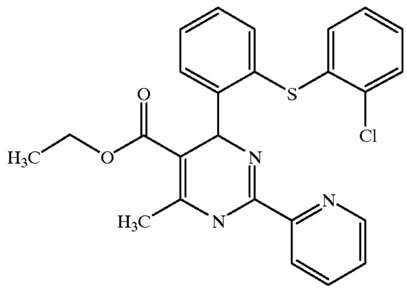 | |
| 73 | x HCl | |
| 74 | x HCl | |
| 75 | x HCl | 166 Z |
| 76 | 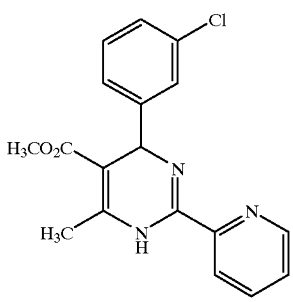 | 122–123 |

TABLE 1-continued

| Ex. No. | Structure | m.p. [° C.] |
| --- | --- | --- |
| 77 | 3-NO2-C6H4 at 4-position, H3CO2C at 5, CH3 at 6, 2-pyridyl at 2, dihydropyrimidine | 179–180 |
| 78 | 2-OCH3-C6H4 at 4-position, H5C2O2C at 5, CH3 at 6, 2-pyridyl at 2, dihydropyrimidine | 132–134 |
| 79 | 2-Cl-C6H4 at 4-position, CO2—(CH2)2—CN at 5, CH3 at 6, 2-pyridyl at 2, dihydropyrimidine | 138–139 |
| 80 | 2-furyl at 4-position, H3CO2C at 5, CH3 at 6, 2-pyridyl at 2, dihydropyrimidine | 122–124 |
| 81 | 2-Cl-C6H4 at 4-position, H5C2O2C at 5, CH3 at 6, 3-pyridyl at 2, dihydropyrimidine | 113–115 |

TABLE 1-continued

| Ex. No. | Structure | m.p. [° C.] |
|---|---|---|
| 82 | 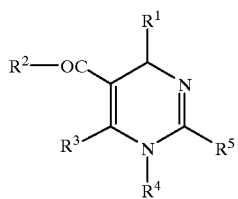 | 105–110 |
| 83 | 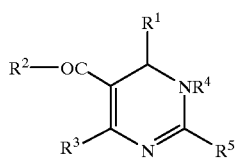 | 131–132 |

*Unless stated otherwise, in the abovementioned structurs, the radical ⟩N⟨ is always the ⟩NH⟨ function.

m.p. = melting point

What is claimed is:

1. A method of treating a hepatitis B infection in a mammal, comprising administering an effective amount of a dihydropyrimidine of the general formula (I)

(I)

or its mesomeric form (Ia)

(Ia)

in which

R¹ is phenyl, furyl, thienyl, triazolyl, pyridyl, cycloalkyl having from 3 to 6 carbon atoms or is a radical of the formula

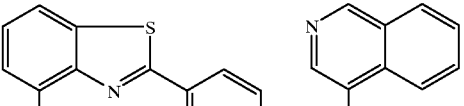

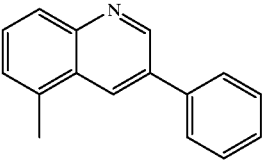

where the abovementioned ring systems are optionally mono- or polysubstituted, identically or differently, by substituents chosen from the group consisting of halogen, trifluoromethyl, nitro, cyano, trifluoromethoxy, carboxyl, hydroxyl, $(C_1-C_6)$-alkoxy, $(C_1-C_6)$-alkoxycarbonyl and $(C_1-C_6)$-alkyl which in turn can be substituted by aryl having from 6 to 10 carbon atoms or halogen, and/or the above ring systems are optionally substituted by groups of the formulae —S—$R^6$, $NR^7R^8$, CO—$NR^9R^{10}$, $SO_2$—$CF_3$, and —A—$CH_2$—$R^{11}$, wherein $R^6$ is phenyl, which is optionally substituted by halogen, $R^7$, $R^8$, $R^9$, and $R^{10}$ are identical or different and are hydrogen, phenyl, hydroxy-substituted phenyl, hydroxyl, $(C_1-C_6)$-acyl or $(C_1-C_6)$-alkyl, which for its part may be substituted by hydroxyl, $(C_1-C_6)$-alkoxycarbonyl, phenyl or hydroxy-substituted phenyl, A is a radical O, S, SO or $SO_2$, $R^{11}$ is phenyl, which is optionally mono- or polysubstituted, identically or differently, by substituents chosen form the group consisting of halogen, nitro, trifluoromethyl, $(C_1-C_6)$-alkyl and $(C_1-C_6)$-alkoxy, $R^2$ is a radical of the formula —$XR^{12}$ or —$NR^{13}R^{14}$, wherein x is a bond or oxygen $R^{12}$ is hydrogen, straight-chain or branched $(C_1-C_6)$-alkoxycarbonyl or a straight-chain, branched or cyclic, saturated or unsaturated $(C_1-C_8)$-hydrocarbon radical, which optionally contains one or two identical or different hetero chain members from the group consisting of O, CO, NH, —NH—$(C_1-C_4)$-alkyl, —N—$((C_1-C_4)$-alkyl$)_2$, S and $SO_2$, and which is optionally substituted by halogen, nitro, cyano, hydroxyl, aryl having from 6 to 10 carbon atoms or aralkyl having from 6 to 10 carbon atoms, heteroaryl or a group of the formula —$NR^{15}R^{16}$, wherein $R^{15}$ and $R^{16}$ are identical or different and are hydrogen, benzyl or $(C_1-C_6)$-alkyl, $R^{13}$ and $R^{14}$ are identical or different and are hydrogen, $(C_1-C_6)$-alkyl or cycloalkyl having from 3 to 6 carbon atoms, $R^3$ is hydrogen, amino or
is a radical of the formula

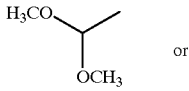

or is formyl, cyano, hydroxy-substituted $(C_1-C_6)$-alkylthio, trifluoromethyl or pyridyl, or is a straight-chain, branched or cyclic, saturated or unsaturated hydrocarbon radical having up to 8 carbon atoms, which is optionally mono- or polysubstituted, identically or differently, by aryloxy having from 6 to 10 carbon atoms, azido, halogen, cyano, hydroxyl, carboxyl, $(C_1-C_6)$-alkoxycarbonyl, $(C_1-C_6)$-alkylthio or $(C_1-C_6)$-alkoxy, which for its part can be substituted by azido or amino, and/or is substituted by triazolyl, which for its part can be substituted up to 3 times by $(C_1-C_6)$-alkoxycarbonyl, and/or can be substituted by groups of the formula —$OSO_{2-H3}$, or $(CO)_a$—$NR^{17}R^{18}$, wherein a is a number 0 or 1, $R^{17}$ and $R^{18}$ are identical or different and are hydrogen or aryl, aralkyl having from 6 to 10 carbon atoms, or are $(C_1-C_6)$-alkyl, which is optionally substituted by $(C_1-C_6)$-alkoxycarbonyl, amino, hydroxyl, phenyl or benzyl, where phenyl or benzyl are optionally mono- or polysubstituted identically or differently, by hydroxyl, carboxyl, $(C_1-C_6)$-alkyl or $(C_1-C_6)$-alkoxy, or $(C_1-C_6)$-alkyl is optionally substituted by groups of the formula NH—CO—$CH_3$ or NH—CO—$CF_3$, or $R^{17}$ and $R^{18}$ together with the nitrogen atom form a morpholine, piperidinyl or pyrrolidinyl ring, or $R^3$ is phenyl, which is optionally substituted by methoxy, or $R^2$ and $R^3$ together form a radical of the formula

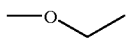

$R^4$ is hydrogen, $(C_1-C_4)$-alkyl, $(C_{2-4})$-alkenyl, benzoyl or is acyl having from 2 to 6 carbon atoms, $R^4$ is hydrogen, methyl, benzoyl or is $(C_2-C_6)$-acyl, $R^5$ is pyridyl, pyrimidyl or pyrazinyl, or a salt thereof to a mammal in need of such treatment.

2. The method according to claim 1, where $R^1$ is phenyl, furyl, thienyl, triazolyl, pyridyl, cyclopentyl or cyclohexyl or is a radical of the formula

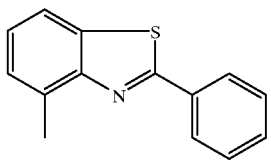 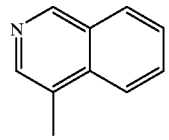

or

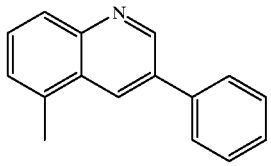

where the abovementioned ring systems are optionally mono- or disubstituted, identically or differently, by substituents chosen from the group consisting of halogen, trifluoromethyl, nitro, $SO_2$—$CF_3$, methyl, cyano, trifluoromethoxy, hydroxyl, carboxyl, methoxycarbonyl or radicals of the formula —CO—NH—$CH_2$—$C(CH_3)_3$, —CO—NH$(CH_2)_2$OH, —CO—NH—$CH_2$—$C_6$—$H_5$, —CO—NH—$CH_2$—$C_6H_5$, —CO—NH—(pOH)—$C_6H_4$, —O—$CH_2$—$C_6H_5$, or —S—pCl—$C_6H_4$, $R_2$ is a radical of the formula —$XR^{12}$ or —$NR^{13}R^{14}$, wherein X is a bond or an oxygen atom, $R^{12}$ is hydrogen, $(C_1$–C4$)$-alkenyl, $(C_1-C_4)$-alkoxycarbonyl or $(C_1-C_4)$-alkyl which are optionally substituted by pyridyl, cyano, phenoxy, benzyl or by a radical of the formula —$NR^{15}R^{16}$, wherein $R^{15}$ and $R^{16}$ are identical or different and are hydrogen, benzyl or $(C_1-C_4)$-alkyl, $R^{13}$ and $R^{14}$ are identical or different and are hydrogen, $(C_1-C_4)$-alkyl or cyclopropyl, $R^3$ is hydrogen, amino or a radical of the formula

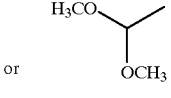

or is formyl, cyano, hydroxy-substituted $(C_1-C_4)$-alkylthio, trifluoromethyl, cyclopropyl or pyridyl, or is (C₁–C₄)-alkyl, which is optionally substituted by halogen, (C₁–C₄)-alkoxycarbonyl, hydroxyl or by triazolyl, which for its part can be substituted up to 3 times by (C₁–C₄)-alkoxycarbonyl, and/or alkyl is optionally substituted by groups of the formulae —OSO₂—CH₃ or (CO)ₐ—NR¹⁷R¹⁸, wherein a is a number 0 or 1, R¹⁷ and R¹⁸ are identical or different and are hydrogen, phenyl or benzyl, or are C₁–C₄-alkyl, which is optionally substituted by (C₁–C₄)-alkoxycarbonyl, amino, hydroxyl, phenyl or benzyl, where phenyl or benzyl are optionally mono- or polysubstituted, identically or differently, by hydroxyl, carboxyl, (C₁–C₄)-alkyl or (C₁–C₄)-alkoxy, and/or (C₁–C₄)-alkyl is optionally substituted by radicals of the formula —NH—CO—CH₃ or —NH—CO—CF₃, or R¹⁷ and R¹⁸ together with the nitrogen atom form a morpholine, piperidinyl or pyrrolidinyl ring, or R³ is phenyl, which is optionally substituted by methoxy, or R² and R³ together form a radical of the formula

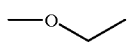

R⁴ is hydrogen, methyl, vinyl or acetyl, and,

R⁵ is pyridyl, pyrimidyl or pyrazinyl.

3. The method according to claim 1 where

R¹ is phenyl, furyl, thienyl, triazolyl, pyridyl, cyclopentyl, cyclohexyl or is a radical of the formula

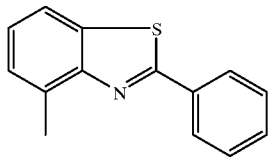 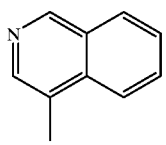

or where said radical is optionally substituted up to twice, identically or differently, by substituents chosen from the group consisting of fluorine, chlorine, bromine, iodine, hydroxyl, trifluoromethyl, nitro, SO₂—CF₃, methyl, cyano, trifluoromethoxy, carboxyl, methoxycarbonyl or radicals of the formula —CO—NH—CH₂—C(CH₃)₃, —CO—NH(CH₂)₂OH, —CO—NH—CH₂—C₆H₅, —CO—NH—C₆H₅, —CO—NH—(pOH)—C₆H₄, —O—CH₂—₆H₅ or —S—pCl—C₆H₄, R² is a radical of the formula —XR¹² or —NR¹³R¹⁴, wherein X is a bond or an oxygen atom, R¹² is hydrogen, (C₁–C₃)-alkenyl, (C₁–C₄)-alkoxycarbonyl or (C₁–C₄)-alkyl, which are optionally substituted by pyridyl, cyano, phenoxy, benzyl or by a radical of the formula —NR¹⁵R¹⁶, wherein R¹⁵ and R¹⁶ are identical or different and are hydrogen or methyl, R¹³ and R¹⁴ are identical or different and are hydrogen, (C₁–C₃)-alkyl or cyclopropyl, R³ is hydrogen, amino or is a radical of the formula

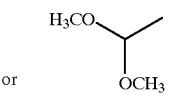

is formyl, cyano, hydroxy-substituted (C₁–C₄)-alkylthio, trifluoromethyl, cyclopropyl or pyridyl, or is (C₁–C₄)-alkyl, which is optionally -substituted by fluorine, chlorine, (C₁–C₃)-alkoxycarbonyl, hydroxyl or by triazolyl, which for its part can be substituted up to 3 times by (C₁–C₃)-alkoxycarbonyl, and/or alkyl is optionally substituted by groups of the formula —OSO₂—CH₃ or (CO)ₐ—NR¹⁷R¹⁸, wherein a is a number 0 or 1, R¹⁷ and R¹⁸ are identical or different and are hydrogen, phenyl or benzyl, or are (C₁–C₃)-alkyl, which is optionally substituted by (C₁–C₃)-alkoxycarbonyl, amino, hydroxyl, phenyl or benzyl, where phenyl or benzyl are optionally mono- or disubstituted, identically or differently, by hydroxyl, carboxyl, (C₁–C₃)-alkyl or (C₁–C₃)-alkoxy, and/or (C₁–C₄)-alkyl is optionally substituted by radicals of the formula —NH—CO¹³ ᶜᴴ₃ or —NH—CO—CF₃, or R¹⁷ and R¹⁸ together with the nitrogen atom form a morpholine, piperidinyl or pyrrolidinyl ring, or R³ is phenyl, which is optionally substituted by methoxy, or R² and R³ together form a radical of the formula

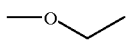

R⁴ is hydrogen, methyl, vinyl or acetyl, and

R⁵ is pyridyl, pyrimidyl or pyrazinyl.

4. The method according to claim 1 where

R¹ is phenyl or triazolyl, which are optionally substituted up to twice, identically or differently, by fluorine, chlorine, bromine or iodine, R² is straight-chain or branched alkoxycarbonyl having up to 4 carbon atoms, R³ is methyl, ethyl or cyclopropyl, or R² and R³ together form a radical of the formula

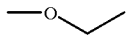

R⁴ is hydrogen, vinyl or acetyl, and

R⁵ is pyridyl.

* * * * *